US007105656B2

(12) United States Patent
Colgan

(10) Patent No.: US 7,105,656 B2
(45) Date of Patent: Sep. 12, 2006

(54) COMPOSITIONS AND METHODS FOR TREATING HEMATOLOGIC MALIGNANCIES AND MULTIPLE DRUG RESISTANCE

(75) Inventor: Sean P. Colgan, North Reading, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 442 days.

(21) Appl. No.: 10/007,255

(22) Filed: Oct. 25, 2001

(65) Prior Publication Data

US 2005/0203036 A1 Sep. 15, 2005

Related U.S. Application Data

(60) Provisional application No. 60/243,542, filed on Oct. 26, 2000.

(51) Int. Cl.
*C07H 21/04* (2006.01)
(52) U.S. Cl. .................................. 536/24.33
(58) Field of Classification Search ................. 514/44; 536/24.5, 24.33
See application file for complete search history.

(56) References Cited

U.S. PATENT DOCUMENTS

| 5,882,914 | A | | 3/1999 | Semenza |
| 5,968,735 | A | * | 10/1999 | Stein et al. .................... 435/6 |
| 6,001,991 | A | | 12/1999 | Dean et al. |
| 6,020,462 | A | | 2/2000 | Semenza |

FOREIGN PATENT DOCUMENTS

| WO | WO 96/39426 A1 | 12/1996 |
| WO | WO 98/14615 A1 | 4/1998 |
| WO | WO 98/20038 | 5/1998 |
| WO | WO 99/09046 A1 | 2/1999 |
| WO | WO 00/36148 | 6/2000 |
| WO | WO 00/69908 A1 | 11/2000 |
| WO | WO 02/02609 A1 | 1/2002 |

OTHER PUBLICATIONS

Verma et al. (Nature 1997, 389:239-242).*
Izquierdo (2004, Cancer Therapy, 1-11).*
Caniggia et al., "Hypoxia-inducible factor-1 mediates the biological effects of oxygen on human trophoblast differentiation through TGFB$_3$," *J. of Clinical Investigation*, vol. 105, No. 5, Mar. 2000, pp. 577-587.
Comerford et al., "Hypoxia-inducible Factor-1-dependent Regulation of the Multidrug Resistance (MDRI) Gene" *Cancer Research*, 62, pp. 3387-3394, Jun. 15, 2002.
Semenza et al., "Hypoxia, Clonal Selection, and the Role of HIF-1 in Tumor Progression." *Critical Reviews in Biochemistry and Molecular Biology*. 35(2); 71-103 (2000).

Semenza et al., "Hypoxia-inducible factor 1: master regulator of O$_2$ homeostasis." *Current Opinion in Genetics & Development*, vol. 8, No. 5. Oct. 1998. pp. 588-594.
Wallace et al. "Induction of multidrug resistance (mdr-1) gene by hypoxia," *Molecular Biology of the Cell*, vol. 11, No. Supplement, Dec. 2000, p. 435a, (abstract).
Communication Relating to the Results of the Partial International Search. PCT/US01/49856, Nov. 18, 2002.
Brown, JM "Exploiting the hypoxic cancer cell: mechanisms and therapeutic strategies," *Molecular Medicine Today*. 6:157-162 (Apr. 2000).
Fardel, O., et al. "The P-glycoprotein multidrug transporter." *Gen. Pharmacol.*, 27(8): 1283-91 (1996).
Jin, S., et al., "Transcriptional regulation of the MDRI gene by histone acetyltransferase and deacetylase is mediated by NF-Y." Molecular and Cellular Biology 18:4377-4384 (1998).
Kaye, SB. "Multidrug resistance: clinical relevance in solid tumors and strategies for circumvention." *Curr Opin Oncol.* 10(suppl. 1):S15-S19 . (1998).
Liang, BC., "Effects of hypoxia on drug resistance phenotype and genotype in human glioma cell lines." J Neuro-Oncology. 29:149-155 (1996).
Ryan, HE., et al. "HIF-1 α is required for solid tumor formation and embryonic vascularization." *EMBO Journal*. 17(11):3005-3015 (1998).
Semenza, GL., et al. "Regulation of mammalian O$_2$ homeostasis by hypoxia-inducible factor I." *Annu. Rev. Cell Dev Biol.* 15:551-78 (1999).
Strauss, BE et al., "The region 3' to the major transcriptional start site of the mdrl downstream promoter mediates activation by a subset of mutant P53 proteins." Biochem Biophys Res Commun. 217(1):333-340 (1995).
Sutherland, RM "Tumor hypoxia and gene expression—implications of malignant progression and therapy." *Acta Oncol.* 37(6):567-74. (1998).
Ueda. K "Expression of a full-length cDNA for the human "MDR1" gene confers resistance to colchicine. doxorubicin, and vinblastine." *Proc. Natl. Acad. Sci. USA* 84:3004-3008 (1987).
Ueda, K.. et al. "Isolation and sequence of the promoter region of the human multidrug resistance (P-glycoprotein) gene." *J. Biol. Chem.* 262(36):17432-17436 (1987).
Ueda, K., et al. "The human multidrug resistance (mdr1) gene." *J. Biol. Chem.* 262(2):505-508 (1987).

(Continued)

*Primary Examiner*—Misook Yu
(74) *Attorney, Agent, or Firm*—Wolf, Greenfield & Sacks, P.C.

(57) ABSTRACT

Methods and compositions are provided for treating a subject having or at risk of developing a hematologic malignancy and/or multiple drug resistance.

4 Claims, No Drawings

OTHER PUBLICATIONS

Ueda, K., et al. "The mdr1 gene, responsible for multidrug-resistance codes for p-glycoprotein." *Biochem Biophys Res Commun.* 141(3):956-962. (1986).

Kretz-Remy et al., "SUMO/sentrin: protein modifiers regulating important cellular functions," *Biochem Cell Biol.*, 77: 299-309 (1999).

Mao et al., "SUMO-1 conjugation to topoisomerase 1: A possible repair response to topoisomerase-mediated DNA damage," *PNAS*, 97, No. 8:4046-4051 (2000).

International Search Report for PCT/US01/49856; Date of Search: Feb. 6, 2003 (Mailed Feb. 17, 2003).

* cited by examiner

SEQUENCE LISTING

```
<160> NUMBER OF SEQ ID NOS: 67

<210> SEQ ID NO 1
<211> LENGTH: 4646
<212> TYPE: DNA
<213> ORGANISM: homo sapiens

<400> SEQUENCE: 1
cctactctat tcagatattc tccagattcc taaagattag agatcatttc tcattctcct      60
aggagtactc acttcaggaa gcaaccagat aaaagagagg tgcaacggaa gccagaacat     120
tcctcctgga aattcaacct gtttcgcagt ttctcgagga atcagcattc agtcaatccg     180
ggccgggagc agtcatctgt ggtgaggctg attggctggg caggaacagc gccggggcgt     240
gggctgagca cagcgcttcg ctctctttgc cacaggaagc ctgagctcat tcgagtagcg     300
gctcttccaa gctcaaagaa gcagaggccg ctgttcgttt cctttaggtc tttccactaa     360
agtcggagta tcttcttcca agatttcacg tcttggtggc cgttccaagg agcgcgaggt     420
```

| | |
|---|---|
| cgggatggat cttgaagggg accgcaatgg aggagcaaag aagaagaact tttttaaact | 480 |
| gaacaataaa agtgaaaaag ataagaagga aaagaaacca actgtcagtg tattttcaat | 540 |
| gtttcgctat tcaaattggc ttgacaagtt gtatatggtg gtgggaactt tggctgccat | 600 |
| catccatggg gctggacttc ctctcatgat gctggtgttt ggagaaatga cagatatctt | 660 |
| tgcaaatgca ggaaatttag aagatctgat gtcaaacatc actaatagaa gtgatatcaa | 720 |
| tgatacaggg ttcttcatga atctggagga agacatgacc aggtatgcct attattacag | 780 |
| tggaattggt gctggggtgc tggttgctgc ttacattcag gtttcatttt ggtgcctggc | 840 |
| agctggaaga caaatacaca aaattagaaa acagttttt catgctataa tgcgacagga | 900 |
| gataggctgg tttgatgtgc acgatgttgg ggagcttaac acccgactta cagatgatgt | 960 |
| ctctaagatt aatgaagtta ttggtgacaa aattggaatg ttctttcagt caatggcaac | 1020 |
| attttcact gggtttatag taggatttac acgtggttgg aagctaaccc ttgtgatttt | 1080 |
| ggccatcagt cctgttcttg gactgtcagc tgctgtctgg gcaaagatac tatcttcatt | 1140 |
| tactgataaa gaactcttag cgtatgcaaa agctggagca gtagctgaag aggtcttggc | 1200 |
| agcaattaga actgtgattg catttggagg acaaaagaaa gaacttgaaa ggtacaacaa | 1260 |
| aaatttagaa gaagctaaaa gaattgggat aaagaaagct attacagcca atatttctat | 1320 |
| aggtgctgct ttcctgctga tctatgcatc ttatgctctg gccttctggt atgggaccac | 1380 |
| cttggtcctc tcagggaat attctattgg acaagtactc actgtattct tttctgtatt | 1440 |
| aattgggct tttagtgttg gacaggcatc tccaagcatt gaagcatttg caaatgcaag | 1500 |
| aggagcagct tatgaaatct tcaagataat tgataataag ccaagtattg acagctattc | 1560 |
| gaagagtggg cacaaaccag ataatattaa gggaaatttg gaattcagaa atgttcactt | 1620 |
| cagttaccca tctcgaaaag aagttaagat cttgaagggc ctgaacctga aggtgcagag | 1680 |
| tgggcagacg gtggcctgg ttggaaacag tggctgtggg aagagcacaa cagtccagct | 1740 |
| gatgcagagg ctctatgacc ccacagaggg gatggtcagt gttgatggac aggatattag | 1800 |
| gaccataaat gtaaggtttc tacgggaaat cattggtgtg gtgagtcagg aacctgtatt | 1860 |
| gtttgccacc acgatagctg aaaacattcg ctatggccgt gaaaatgtca ccatggatga | 1920 |
| gattgagaaa gctgtcaagg aagccaatgc ctatgacttt atcatgaaac tgcctcataa | 1980 |
| atttgacacc ctggttggag agagggggc ccagttgagt ggtgggcaga agcagaggat | 2040 |
| cgccattgca cgtgccctgg ttcgcaaccc caagatcctc ctgctggatg aggccacgtc | 2100 |
| agccttggac acagaaagcg aagcagtggt tcaggtggct ctggataagg ccagaaaagg | 2160 |
| tcggaccacc attgtgatag ctcatcgttt gtctacagtt cgtaatgctg acgtcatcgc | 2220 |
| tggtttcgat gatggagtca ttgtggagaa aggaaatcat gatgaactca tgaaagagaa | 2280 |
| aggcatttac ttcaaacttg tcacaatgca gacagcagga atgaagttga attagaaaa | 2340 |
| tgcagctgat gaatccaaaa gtgaaattga tgccttggaa atgtcttcaa atgattcaag | 2400 |
| atccagtcta ataagaaaaa gatcaactcg taggagtgtc cgtggatcac aagcccaaga | 2460 |
| cagaaagctt agtaccaaag aggctctgga tgaaagtata cctccagttt ccttttggag | 2520 |
| gattatgaag ctaaatttaa ctgaatggcc ttattttgtt gttggtgtat tttgtgccat | 2580 |
| tataaatgga ggcctgcaac cagcatttgc aataatattt tcaaagatta tagggggtttt | 2640 |
| tacaagaatt gatgatcctg aaacaaaacg acagaatagt aacttgtttt cactattgtt | 2700 |
| tctagccctt ggaattattt cttttattac attttccctt cagggttca catttggcaa | 2760 |
| agctggagag atcctcacca agcggctccg atacatggtt ttccgatcca tgctcagaca | 2820 |

-continued

```
ggatgtgagt tggtttgatg accctaaaaa caccactgga gcattgacta ccaggctcgc   2880
caatgatgct gctcaagtta aagggctat aggttccagg cttgctgtaa ttacccagaa    2940
tatagcaaat cttgggacag gaataattat atccttcatc tatggttggc aactaacact   3000
gttactctta gcaattgtac ccatcattgc aatagcagga gttgttgaaa tgaaaatgtt   3060
gtctggacaa gcactgaaag ataagaaaga actagaaggt gctgggaaga tcgctactga   3120
agcaatagaa aacttccgaa ccgttgtttc tttgactcag gagcagaagt ttgaacatat   3180
gtatgctcag agtttgcagg taccatacag aaactctttg aggaaagcac acatctttgg   3240
aattacattt tccttcaccc aggcaatgat gtattttttcc tatgctggat gtttccggtt   3300
tggagcctac ttggtggcac ataaactcat gagctttgag gatgttctgt tagtattttc   3360
agctgttgtc tttggtgcca tggccgtggg gcaagtcagt tcatttgctc ctgactatgc   3420
caaagccaaa atatcagcag cccacatcat catgatcatt gaaaaaaccc ctttgattga   3480
cagctacagc acggaaggcc taatgccgaa cacattggaa ggaaatgtca catttggtga   3540
agttgtattc aactatccca cccgaccgga catcccagtg cttcagggac tgagcctgga   3600
ggtgaagaag ggccagacgc tggctctggt gggcagcagt ggctgtggga gagcacagt    3660 ggtccagctc ctggagcggt tctacgaccc cttggcaggg aaagtgctgc ttgatggcaa   3720
agaaataaag cgactgaatg ttcagtggct ccgagcacac ctgggcatcg tgtcccagga   3780
gcccatcctg tttgactgca gcattgctga gaacattgcc tatggagaca cagccgggt    3840 ggtgtcacag gaagagatcg tgagggcagc aaaggaggcc aacatacatg ccttcatcga   3900
gtcactgcct aataaatata gcactaaagt aggagacaaa ggaactcagc tctctggtgg   3960
ccagaaacaa cgcattgcca tagctcgtgc ccttgttaga cagcctcata ttttgctttt   4020
ggatgaagcc acgtcagctc tggatacaga aagtgaaaag gttgtccaag aagccctgga   4080
caaagccaga gaaggccgca cctgcattgt gattgctcac cgcctgtcca ccatccagaa   4140
tgcagactta atagtggtgt tcagaatgg cagagtcaag gagcatggca cgcatcagca   4200
gctgctggca cagaaaggca tctatttttc aatggtcagt gtccaggctg aacaaagcg    4260 ccagtgaact ctgactgtat gagatgttaa atactttta atatttgttt agatatgaca    4320
tttattcaaa gttaaaagca aacacttaca gaattatgaa gaggtatctg tttaacattt    4380
cctcagtcaa gttcagagtc ttcagagact tcgtaattaa aggaacagag tgagagacat   4440
catcaagtgg agagaaatca tagtttaaac tgcattataa attttataac agaattaaag   4500
tagattttaa aagataaaat gtgtaatttt gtttatattt tcccatttgg actgtaactg   4560
actgccttgc taaagatta tagaagtagc aaaaagtatt gaaatgtttg cataaagtgt    4620
ctataataaa actaaacttt catgtg                                        4646
```

<210> SEQ ID NO 2
<211> LENGTH: 1280
<212> TYPE: PRT
<213> ORGANISM: homo sapiens

<400> SEQUENCE: 2

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45
```

-continued

```
Leu Tyr Met Val Val Gly Thr Leu Ala Ala Ile Ile His Gly Ala Gly
 50                  55                  60

Leu Pro Leu Met Met Leu Val Phe Gly Glu Met Thr Asp Ile Phe Ala
 65                  70                  75                  80

Asn Ala Gly Asn Leu Glu Asp Leu Met Ser Asn Ile Thr Asn Arg Ser
                 85                  90                  95

Asp Ile Asn Asp Thr Gly Phe Phe Met Asn Leu Glu Glu Asp Met Thr
            100                 105                 110

Arg Tyr Ala Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Val Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460
```

-continued

```
Phe Leu Arg Glu Ile Ile Gly Val Val Ser Gln Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
            515                 520                 525

Ala Gln Leu Ser Gly Gly Gln Lys Gln Arg Ile Ala Ile Ala Arg Ala
        530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
                580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
        610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
                660                 665                 670

Arg Gly Ser Gln Ala Gln Asp Arg Lys Leu Ser Thr Lys Glu Ala Leu
            675                 680                 685

Asp Glu Ser Ile Pro Pro Val Ser Phe Trp Arg Ile Met Lys Leu Asn
        690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
                740                 745                 750

Asn Leu Phe Ser Leu Leu Phe Leu Ala Leu Gly Ile Ile Ser Phe Ile
            755                 760                 765

Thr Phe Phe Leu Gln Gly Phe Thr Phe Gly Lys Ala Gly Glu Ile Leu
        770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
                820                 825                 830

Leu Ala Val Ile Thr Gln Asn Ile Ala Asn Leu Gly Thr Gly Ile Ile
            835                 840                 845

Ile Ser Phe Ile Tyr Gly Trp Gln Leu Thr Leu Leu Leu Leu Ala Ile
        850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
```

-continued

```
                885                 890                 895
Ala Thr Glu Ala Ile Glu Asn Phe Arg Thr Val Val Ser Leu Thr Gln
            900                 905                 910
Glu Gln Lys Phe Glu His Met Tyr Ala Gln Ser Leu Gln Val Pro Tyr
            915                 920                 925
Arg Asn Ser Leu Arg Lys Ala His Ile Phe Gly Ile Thr Phe Ser Phe
        930                 935                 940
Thr Gln Ala Met Met Tyr Phe Ser Tyr Ala Gly Cys Phe Arg Phe Gly
945                 950                 955                 960
Ala Tyr Leu Val Ala His Lys Leu Met Ser Phe Glu Asp Val Leu Leu
                965                 970                 975
Val Phe Ser Ala Val Val Phe Gly Ala Met Ala Val Gly Gln Val Ser
            980                 985                 990
Ser Phe Ala Pro Asp Tyr Ala Lys Ala Lys Ile Ser Ala Ala His Ile
        995                 1000                1005
Ile Met Ile Ile Glu Lys Thr Pro Leu Ile Asp Ser Tyr Ser Thr
    1010                1015                1020
Glu Gly Leu Met Pro Asn Thr Leu Glu Gly Asn Val Thr Phe Gly
    1025                1030                1035
Glu Val Val Phe Asn Tyr Pro Thr Arg Pro Asp Ile Pro Val Leu
    1040                1045                1050
Gln Gly Leu Ser Leu Glu Val Lys Lys Gly Gln Thr Leu Ala Leu
    1055                1060                1065
Val Gly Ser Ser Gly Cys Gly Lys Ser Thr Val Val Gln Leu Leu
    1070                1075                1080
Glu Arg Phe Tyr Asp Pro Leu Ala Gly Lys Val Leu Leu Asp Gly
    1085                1090                1095
Lys Glu Ile Lys Arg Leu Asn Val Gln Trp Leu Arg Ala His Leu
    1100                1105                1110
Gly Ile Val Ser Gln Glu Pro Ile Leu Phe Asp Cys Ser Ile Ala
    1115                1120                1125
Glu Asn Ile Ala Tyr Gly Asp Asn Ser Arg Val Val Ser Gln Glu
    1130                1135                1140
Glu Ile Val Arg Ala Ala Lys Glu Ala Asn Ile His Ala Phe Ile
    1145                1150                1155
Glu Ser Leu Pro Asn Lys Tyr Ser Thr Lys Val Gly Asp Lys Gly
    1160                1165                1170
Thr Gln Leu Ser Gly Gly Gln Lys Gln Arg Ile Ala Ile Ala Arg
    1175                1180                1185
Ala Leu Val Arg Gln Pro His Ile Leu Leu Leu Asp Glu Ala Thr
    1190                1195                1200
Ser Ala Leu Asp Thr Glu Ser Glu Lys Val Val Gln Glu Ala Leu
    1205                1210                1215
Asp Lys Ala Arg Glu Gly Arg Thr Cys Ile Val Ile Ala His Arg
    1220                1225                1230
Leu Ser Thr Ile Gln Asn Ala Asp Leu Ile Val Val Phe Gln Asn
    1235                1240                1245
Gly Arg Val Lys Glu His Gly Thr His Gln Gln Leu Leu Ala Gln
    1250                1255                1260
Lys Gly Ile Tyr Phe Ser Met Val Ser Val Gln Ala Gly Thr Lys
    1265                1270                1275
Arg Gln
    1280
```

<210> SEQ ID NO 3
<211> LENGTH: 3678
<212> TYPE: DNA
<213> ORGANISM: homo sapiens

<400> SEQUENCE: 3

| | | | | | |
|---|---|---|---|---|---|
| gtgaagacat | cgcggggacc | gattcaccat | ggagggcgcc | ggcggcgcga | acgacaagaa | 60 |
| aaagataagt | tctgaacgtc | gaaaagaaaa | gtctcgagat | gcagccagat | ctcggcgaag | 120 |
| taaagaatct | gaagtttttt | atgagcttgc | tcatcagttg | ccacttccac | ataatgtgag | 180 |
| ttcgcatctt | gataaggcct | ctgtgatgag | gcttaccatc | agctatttgc | gtgtgaggaa | 240 |
| acttctggat | gctggtgatt | tggatattga | agatgacatg | aaagcacaga | tgaattgctt | 300 |
| ttatttgaaa | gccttggatg | gttttgttat | ggttctcaca | gatgatggtg | acatgattta | 360 |
| catttctgat | aatgtgaaca | atacatggg | attaactcag | tttgaactaa | ctggacacag | 420 |
| tgtgtttgat | tttactcatc | catgtgacca | tgaggaaatg | agagaaatgc | ttacacacag | 480 |
| aaatggcctt | gtgaaaaagg | gtaaagaaca | aacacacag | cgaagctttt | ttctcagaat | 540 |
| gaagtgtacc | ctaactagcc | gaggaagaac | tatgaacata | aagtctgcaa | catggaaggt | 600 |
| attgcactgc | acaggccaca | ttcacgtata | tgataccaac | agtaaccaac | ctcagtgtgg | 660 |
| gtataagaaa | ccacctatga | cctgcttggt | gctgatttgt | gaacccattc | ctcacccatc | 720 |
| aaatattgaa | attcctttag | atagcaagac | tttcctcagt | cgacacagcc | tggatatgaa | 780 |
| attttcttat | tgtgatgaaa | gaattaccga | attgatggga | tatgagccag | aagaactttt | 840 |
| aggccgctca | atttatgaat | attatcatgc | tttggactct | gatcatctga | ccaaaactca | 900 |
| tcatgatatg | tttactaaag | gacaagtcac | cacaggacag | tacaggatgc | ttgccaaaag | 960 |
| aggtggatat | gtctgggttg | aaactcaagc | aactgtcata | taacaccca | agaattctca | 1020 |
| accacagtgc | attgtatgtg | tgaattacgt | tgtgagtggt | attattcagc | acgacttgat | 1080 |
| tttctcccctt | caacaaacag | aatgtgtcct | taaaccggtt | gaatcttcag | atatgaaaat | 1140 |
| gactcagcta | ttcaccaaag | ttgaatcaga | agatacaagt | agcctctttg | acaaacttaa | 1200 |
| gaaggaaccct | gatgctttaa | ctttgctggc | cccagccgct | ggagacacaa | tcatatcttt | 1260 |
| agattttggc | agcaacgaca | cagaaactga | tgaccagcaa | cttgaggaag | taccattata | 1320 |
| taatgatgta | atgctcccct | cacccaacga | aaaattacag | aatataaatt | tggcaatgtc | 1380 |
| tccattaccc | accgctgaaa | cgccaaagcc | acttcgaagt | agtgctgacc | ctgcactcaa | 1440 |
| tcaagaagtt | gcattaaaat | tagaaccaaa | tccagagtca | ctggaacttt | cttttaccat | 1500 |
| gccccagatt | caggatcaga | cacctagtcc | ttccgatgga | agcactagac | aaagttcacc | 1560 |
| tgagcctaat | agtcccagtg | aatattgttt | ttatgtggat | agtgatatgg | tcaatgaatt | 1620 |
| caagttggaa | ttggtagaaa | aactttttgc | tgaagcacaa | gaagcaaaga | acccattttc | 1680 |
| tactcaggac | acagatttag | acttggagat | gttagctccc | tatatcccaa | tggatgatga | 1740 |
| cttccagtta | cgttccttcg | atcagttgtc | accattagaa | agcagttccg | caagccctga | 1800 |
| aagcgcaagt | cctcaaagca | cagttacagt | attccagcag | actcaaatac | aagaacctac | 1860 |
| tgctaatgcc | accactacca | ctgccaccac | tgatgaatta | aaaacagtga | caaaagaccg | 1920 |
| tatggaagac | attaaaatat | tgattgcatc | tccatctcct | acccacatac | ataaagaaac | 1980 |
| tactagtgcc | acatcatcac | catatagaga | tactcaaagt | cggacagcct | caccaaacag | 2040 |
| agcaggaaaa | ggagtcatag | aacagacaga | aaaatctcat | ccaagaagcc | ctaacgtgtt | 2100 |

-continued

```
atctgtcgct ttgagtcaaa gaactacagt tcctgaggaa gaactaaatc caaagatact    2160
agctttgcag aatgctcaga gaaagcgaaa atggaacat gatggttcac ttttcaagc      2220 agtaggaatt ggaacattat tacagcagcc agacgatcat gcagctacta catcactttc    2280
ttggaaacgt gtaaaaggat gcaaatctag tgaacagaat ggaatggagc aaaagacaat    2340
tattttaata ccctctgatt tagcatgtag actgctgggg caatcaatgg atgaaagtgg    2400
attaccacag ctgaccagtt atgattgtga agttaatgct cctatacaag gcagcagaaa    2460
cctactgcag ggtgaagaat tactcagagc tttggatcaa gttaactgag cttttttctta   2520 atttcattcc ttttttttgga cactggtggc tcactaccta agcagtcta tttatatttt    2580 ctacatctaa ttttagaagc ctggctacaa tactgcacaa acttggttag ttcaatttt     2640 gatcccttt ctacttaatt tacattaatg ctctttttta gtatgttctt taatgctgga    2700
tcacagacag ctcatttct cagttttttg gtatttaaac cattgcattg cagtagcatc    2760
attttaaaaa atgcaccttt ttatttattt attttggct agggagttta tccctttttc    2820
gaattatttt taagaagatg ccaatataat ttttgtaaga aggcagtaac ctttcatcat    2880
gatcataggc agttgaaaaa ttttacacc tttttttca cattttacat aaataataat      2940
gctttgccag cagtacgtgg tagccacaat tgcacaatat attttcttaa aaaataccag    3000
cagttactca tggaatatat tctgcgttta taaaactagt ttttaagaag aaattttttt    3060
tggcctatga aattgttaaa cctggaacat gacattgtta atcatataat aatgattctt    3120
aaatgctgta tggtttatta tttaaatggg taaagccatt tacataatat agaaagatat    3180
gcatatatct agaaggtatg tggcatttat ttggataaaa ttctcaattc agagaaatca    3240
tctgatgttt ctatagtcac tttgccagct caaaagaaaa caataccta tgtagttgtg    3300 gaagtttatg ctaatattgt gtaactgata ttaaacctaa atgttctgcc taccctgttg    3360
gtataaagat attttgagca gactgtaaac aagaaaaaaa aaatcatgca ttcttagcaa    3420
aattgcctag tatgttaatt tgctcaaaat acaatgtttg attttatgca ctttgtcgct    3480
attaacatcc ttttttcat gtagatttca ataattgagt aattttagaa gcattatttt    3540
aggaatatat agttgtcaca gtaaatatct tgttttttct atgtacattg tacaaatttt    3600
tcattccttt tgctctttgt ggttggatct aacactaact gtattgtttt gttacatcaa    3660
ataaacatct tctgtggga                                                  3678
```

<210> SEQ ID NO 4
<211> LENGTH: 826
<212> TYPE: PRT
<213> ORGANISM: homo sapiens
<400> SEQUENCE: 4

```
Met Glu Gly Ala Gly Gly Ala Asn Asp Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95
```

-continued

```
Asp Gly Phe Val Met Val Leu Thr Asp Asp Gly Asp Met Ile Tyr Ile
            100                 105                 110
Ser Asp Asn Val Asn Lys Tyr Met Gly Leu Thr Gln Phe Glu Leu Thr
            115                 120                 125
Gly His Ser Val Phe Asp Phe Thr His Pro Cys Asp His Glu Glu Met
            130                 135                 140
Arg Glu Met Leu Thr His Arg Asn Gly Leu Val Lys Lys Gly Lys Glu
145                 150                 155                 160
Gln Asn Thr Gln Arg Ser Phe Phe Leu Arg Met Lys Cys Thr Leu Thr
                165                 170                 175
Ser Arg Gly Arg Thr Met Asn Ile Lys Ser Ala Thr Trp Lys Val Leu
            180                 185                 190
His Cys Thr Gly His Ile His Val Tyr Asp Thr Asn Ser Asn Gln Pro
            195                 200                 205
Gln Cys Gly Tyr Lys Lys Pro Pro Met Thr Cys Leu Val Leu Ile Cys
            210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
                245                 250                 255
Glu Arg Ile Thr Glu Leu Met Gly Tyr Glu Pro Glu Glu Leu Leu Gly
            260                 265                 270
Arg Ser Ile Tyr Glu Tyr Tyr His Ala Leu Asp Ser Asp His Leu Thr
            275                 280                 285
Lys Thr His His Asp Met Phe Thr Lys Gly Gln Val Thr Thr Gly Gln
            290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
                325                 330                 335
Cys Val Asn Tyr Val Val Ser Gly Ile Ile Gln His Asp Leu Ile Phe
            340                 345                 350
Ser Leu Gln Gln Thr Glu Cys Val Leu Lys Pro Val Glu Ser Ser Asp
            355                 360                 365
Met Lys Met Thr Gln Leu Phe Thr Lys Val Glu Ser Glu Asp Thr Ser
370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
Asp Thr Glu Thr Asp Asp Gln Gln Leu Glu Glu Val Pro Leu Tyr Asn
            420                 425                 430
Asp Val Met Leu Pro Ser Pro Asn Glu Lys Leu Gln Asn Ile Asn Leu
            435                 440                 445
Ala Met Ser Pro Leu Pro Thr Ala Glu Thr Pro Lys Pro Leu Arg Ser
450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
Gln Thr Pro Ser Pro Ser Asp Gly Ser Thr Arg Gln Ser Ser Pro Glu
            500                 505                 510
```

```
Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Ala Thr Thr Asp Glu Leu
610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
                740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
            770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 5
<211> LENGTH: 2616
<212> TYPE: DNA
<213> ORGANISM: homo sapiens

<400> SEQUENCE: 5
atggcggctc ctcccactgg ggggggggtg gcgcggcggc ggtggcatct gcggccatgg      60
cggcgactac tgccaacccc gaaatgacat cagatgtacc atcactgggt ccagccattg     120
cctctggaaa ctctggacct ggaattcaag gtggaggagc cattgtccag agggctatta     180
agcggcgacc agggctggat tttgatgatg atggagaagg gaacagtaaa tttttgaggt     240
gtgatgatga tcagatgtct aacgataagg agcggtttgc caggtcggat gatgagcaga     300
gctctgcgga taagagagag cttgccaggg aaaatcacag tgaaattgaa cggcggcgac     360
```

-continued

```
ggaacaagat gacagcctac atcacagaac tgtcagatat ggtacccacc tgtagtgccc    420
tggctcgaaa accagacaag ctaaccatct tacgcatggc agtttctcac atgaagtcct    480
tgcggggaac tggcaacaca tccactgatg gctcctataa gccgtctttc ctcactgatc    540
aggaactgaa acatttgatc ttggaggcag cagatggctt tctgtttatt gtctcatgtg    600
agacaggcag ggtggtgtat gtgtctgact ccgtgactcc tgttttgaac cagccacagt    660
ctgaatggtt tggcagcaca ctctatgatc aggtgcaccc agatgatgtg gataaacttc    720
gtgagcagct ttccacttca gaaaatgccc tgacagggcg tatcctggat ctaaagactg    780
gaacagtgaa aaggaaggt cagcagtctt ccatgagaat gtgtatgggc tcaaggagat    840
cgtttatttg ccgaatgagg tgtggcagta gctctgtgga cccagtttct gtgaataggc    900
tgagctttgt gaggaacaga tgcaggaatg gacttggctc tgtaaaggat ggggaacctc    960
acttcgtggt ggtccactgc acaggctaca tcaaggcctg ccccagca ggtgtttccc    1020 tcccagatga tgacccagag gctggccagg gaagcaagtt ttgcctagtg gccattggca    1080
gattgcaggt aactagttct cccaactgta cagacatgag taatgtttgt caaccaacag    1140
agttcatctc ccgacacaac attgagggta tcttcacttt tgtggatcac cgctgtgtgg    1200
ctactgttgg ctaccagcca caggaactct taggaaagaa tattgtagaa ttctgtcatc    1260
ctgaagacca gcagcttcta agagacagct tccaacaggt agtgaaatta aaaggccaag    1320
tgctgtctgt catgttccgg ttccggtcta agaaccaaga atggctctgg atgagaacca    1380
gctcctttac tttccagaac ccttactcag atgaaattga gtacatcatc tgtaccaaca    1440
ccaatgtgaa gaactctagc caagaaccac ggcctacact ctccaacaca atccagaggc    1500
cacaactagg tcccacagct aatttacccc tggagatggg ctcaggacag ctggcaccca    1560
ggcagcagca acagcaaaca gaattggaca tggtaccagg aagagatgga ctggccagct    1620
acaatcattc ccaggtggtt cagcctgtga caaccacagg accagaacac agcaagcccc    1680
ttgagaagtc agatggtttta ttrgcccagg atagagatcc aagattttca gaaatctatc    1740
acaacatcaa tgcggatcag agtaaaggca tctcctccag cactgtccct gccacccaac    1800
agctattctc ccagggcaac acattccctc ctaccccccg gccggcagag aatttcagga    1860
atagtggcct agcccctcct gtaaccattg tccagccatc agcttctgca ggacagatgt    1920
tggcccagat ttcccgccac tccaacccca cccaaggagc aaccccaact tggacccta    1980 ctacccgctc aggcttttct gcccagcagg tggctaccca ggctactgct aagactcgta    2040
cttcccagtt tggtgtgggc agctttcaga ctccatcctc cttcagctcc atgtccctcc    2100
ctggtgcccc aactgcatcg cctggtgctg ctgcctaccc tagtctcacc aatcgtggat    2160
ctaactttgc tcctgagact ggacagactg caggacaatt ccagacacgg acagcagagg    2220
gtgtgggtgt ctggccacag tggcagggcc agcagcctca tcatcgttca agttctagtg    2280
agcaacatgt tcaacaaccg ccagcacagc aacctggcca gcctgaggtc ttccaggaga    2340
tgctgtccat gctgggagat cagagcaaca gctacaacaa tgaagaattc cctgatctaa    2400
ctatgtttcc ccccttttca gaatagaact attggggtga ggataagggg tgggggagaa    2460
aaaatcactg tttgttttta aaagcaaat ctttctgtaa acagaataaa agttcctctc    2520
ccttcccttc cctcacccct gacatgtacc cccttccct tctggctgtt cccctgctct    2580
gttgcctcct aagtaacat ttataaaaaa aaaaaa    2616
```

<210> SEQ ID NO 6

```
<211> LENGTH: 789
<212> TYPE: PRT
<213> ORGANISM: homo sapiens

<400> SEQUENCE: 6

Met Ala Ala Thr Thr Ala Asn Pro Glu Met Thr Ser Asp Val Pro Ser
1               5                   10                  15

Leu Gly Pro Ala Ile Ala Ser Gly Asn Ser Gly Pro Gly Ile Gln Gly
            20                  25                  30

Gly Gly Ala Ile Val Gln Arg Ala Ile Lys Arg Arg Pro Gly Leu Asp
        35                  40                  45

Phe Asp Asp Asp Gly Glu Gly Asn Ser Lys Phe Leu Arg Cys Asp Asp
50                  55                  60

Asp Gln Met Ser Asn Asp Lys Glu Arg Phe Ala Arg Ser Asp Asp Glu
65                  70                  75                  80

Gln Ser Ser Ala Asp Lys Glu Arg Leu Ala Arg Glu Asn His Ser Glu
                85                  90                  95

Ile Glu Arg Arg Arg Arg Asn Lys Met Thr Ala Tyr Ile Thr Glu Leu
            100                 105                 110

Ser Asp Met Val Pro Thr Cys Ser Ala Leu Ala Arg Lys Pro Asp Lys
        115                 120                 125

Leu Thr Ile Leu Arg Met Ala Val Ser His Met Lys Ser Leu Arg Gly
130                 135                 140

Thr Gly Asn Thr Ser Thr Asp Gly Ser Tyr Lys Pro Ser Phe Leu Thr
145                 150                 155                 160

Asp Gln Glu Leu Lys His Leu Ile Leu Glu Ala Ala Asp Gly Phe Leu
                165                 170                 175

Phe Ile Val Ser Cys Glu Thr Gly Arg Val Val Tyr Val Ser Asp Ser
            180                 185                 190

Val Thr Pro Val Leu Asn Gln Pro Gln Ser Glu Trp Phe Gly Ser Thr
        195                 200                 205

Leu Tyr Asp Gln Val His Pro Asp Asp Val Asp Lys Leu Arg Glu Gln
210                 215                 220

Leu Ser Thr Ser Glu Asn Ala Leu Thr Gly Arg Ile Leu Asp Leu Lys
225                 230                 235                 240

Thr Gly Thr Val Lys Lys Glu Gly Gln Gln Ser Ser Met Arg Met Cys
                245                 250                 255

Met Gly Ser Arg Arg Ser Phe Ile Cys Arg Met Arg Cys Gly Ser Ser
            260                 265                 270

Ser Val Asp Pro Val Ser Val Asn Arg Leu Ser Phe Val Arg Asn Arg
        275                 280                 285

Cys Arg Asn Gly Leu Gly Ser Val Lys Asp Gly Glu Pro His Phe Val
    290                 295                 300

Val Val His Cys Thr Gly Tyr Ile Lys Ala Trp Pro Pro Ala Gly Val
305                 310                 315                 320

Ser Leu Pro Asp Asp Pro Glu Ala Gly Gln Gly Ser Lys Phe Cys
                325                 330                 335

Leu Val Ala Ile Gly Arg Leu Gln Val Thr Ser Ser Pro Asn Cys Thr
            340                 345                 350

Asp Met Ser Asn Val Cys Gln Pro Thr Glu Phe Ile Ser Arg His Asn
        355                 360                 365

Ile Glu Gly Ile Phe Thr Phe Val Asp His Arg Cys Val Ala Thr Val
    370                 375                 380

Gly Tyr Gln Pro Gln Glu Leu Leu Gly Lys Asn Ile Val Glu Phe Cys
```

```
                385                 390                 395                 400
His Pro Glu Asp Gln Gln Leu Leu Arg Asp Ser Phe Gln Gln Val Val
                    405                 410                 415
Lys Leu Lys Gly Gln Val Leu Ser Val Met Phe Arg Phe Arg Ser Lys
                420                 425                 430
Asn Gln Glu Trp Leu Trp Met Arg Thr Ser Ser Phe Thr Phe Gln Asn
            435                 440                 445
Pro Tyr Ser Asp Glu Ile Glu Tyr Ile Ile Cys Thr Asn Thr Asn Val
        450                 455                 460
Lys Asn Ser Ser Gln Glu Pro Arg Pro Thr Leu Ser Asn Thr Ile Gln
465                 470                 475                 480
Arg Pro Gln Leu Gly Pro Thr Ala Asn Leu Pro Leu Glu Met Gly Ser
                485                 490                 495
Gly Gln Leu Ala Pro Arg Gln Gln Gln Gln Thr Glu Leu Asp Met
            500                 505                 510
Val Pro Gly Arg Asp Gly Leu Ala Ser Tyr Asn His Ser Gln Val Val
        515                 520                 525
Gln Pro Val Thr Thr Thr Gly Pro Glu His Ser Lys Pro Leu Glu Lys
    530                 535                 540
Ser Asp Gly Leu Phe Ala Gln Asp Arg Asp Pro Arg Phe Ser Glu Ile
545                 550                 555                 560
Tyr His Asn Ile Asn Ala Asp Gln Ser Lys Gly Ile Ser Ser Thr
                565                 570                 575
Val Pro Ala Thr Gln Gln Leu Phe Ser Gln Gly Asn Thr Phe Pro Pro
            580                 585                 590
Thr Pro Arg Pro Ala Glu Asn Phe Arg Asn Ser Gly Leu Ala Pro Pro
        595                 600                 605
Val Thr Ile Val Gln Pro Ser Ala Ser Ala Gly Gln Met Leu Ala Gln
    610                 615                 620
Ile Ser Arg His Ser Asn Pro Thr Gln Gly Ala Thr Pro Thr Trp Thr
625                 630                 635                 640
Pro Thr Thr Arg Ser Gly Phe Ser Ala Gln Gln Val Ala Thr Gln Ala
                645                 650                 655
Thr Ala Lys Thr Arg Thr Ser Gln Phe Gly Val Gly Ser Phe Gln Thr
            660                 665                 670
Pro Ser Ser Phe Ser Ser Met Ser Leu Pro Gly Ala Pro Thr Ala Ser
        675                 680                 685
Pro Gly Ala Ala Ala Tyr Pro Ser Leu Thr Asn Arg Gly Ser Asn Phe
    690                 695                 700
Ala Pro Glu Thr Gly Gln Thr Ala Gly Gln Phe Gln Thr Arg Thr Ala
705                 710                 715                 720
Glu Gly Val Gly Val Trp Pro Gln Trp Gln Gly Gln Pro His His
                725                 730                 735
Arg Ser Ser Ser Glu Gln His Val Gln Gln Pro Ala Gln Gln
            740                 745                 750
Pro Gly Gln Pro Glu Val Phe Gln Glu Met Leu Ser Met Leu Gly Asp
        755                 760                 765
Gln Ser Asn Ser Tyr Asn Asn Glu Glu Phe Pro Asp Leu Thr Met Phe
    770                 775                 780
Pro Pro Phe Ser Glu
785

<210> SEQ ID NO 7
```

```
<211> LENGTH: 816
<212> TYPE: DNA
<213> ORGANISM: homo sapiens

<400> SEQUENCE: 7
gatttgtaaa cccggagcg aggttctgct tacccgaggc cgctgctgtg cggagacccc      60
cgggtgaagc caccgtcatc atgtctgacc aggaggcaaa accttcaact gaggacttgg    120
gggataagaa ggaaggtgaa tatattaaac tcaaagtcat tggacaggat agcagtgaga    180
ttcacttcaa agtgaaaatg acaacacatc tcaagaaact caaagaatca tactgtcaaa    240
gacagggtgt tccaatgaat tcactcaggt ttctctttga gggtcagaga attgctgata    300
atcatactcc aaaagaactg ggaatggagg aagaagatgt gattgaagtt tatcaggaac    360
aaacgggggg tcattcaaca gtttagatat tctttttatt ttttttcttt tccctcaatc    420
cttttttatt tttaaaaata gttcttttgt aatgtggtgt tcaaaacgga attgaaaact    480
ggcaccccat ctctttgaaa catctggtaa tttgaattct agtgctcatt attcattatt    540
gtttgttttc attgtgctga ttttttggtga tcaagcctca gtccccttca tattaccctc    600 tccttttttaa aaattacgtg tgcacagaga ggtcaccttt ttcaggacat tgcattttca    660
ggcttgtggt gataaataag atcgaccaat gcaagtgttc ataatgactt tccaattggc    720
cctgatgttc tagcatgtga ttacttcact ccctggactg tgactttcag tgggagatgg    780
aattttttcc agaaaaactg aactgtggaa aaatga                              816

<210> SEQ ID NO 8
<211> LENGTH: 101
<212> TYPE: PRT
<213> ORGANISM: homo sapiens

<400> SEQUENCE: 8

Met Ser Asp Gln Glu Ala Lys Pro Ser Thr Glu Asp Leu Gly Asp Lys
 1               5                  10                  15

Lys Glu Gly Glu Tyr Ile Lys Leu Lys Val Ile Gly Gln Asp Ser Ser
             20                  25                  30

Glu Ile His Phe Lys Val Lys Met Thr Thr His Leu Lys Lys Leu Lys
         35                  40                  45

Glu Ser Tyr Cys Gln Arg Gln Gly Val Pro Met Asn Ser Leu Arg Phe
     50                  55                  60

Leu Phe Glu Gly Gln Arg Ile Ala Asp Asn His Thr Pro Lys Glu Leu
 65                  70                  75                  80

Gly Met Glu Glu Glu Asp Val Ile Glu Val Tyr Gln Glu Gln Thr Gly
                 85                  90                  95

Gly His Ser Thr Val
            100

<210> SEQ ID NO 9
<211> LENGTH: 24
<212> TYPE: DNA
<213> ORGANISM: homo sapiens

<400> SEQUENCE: 9
cttatgtaga cacgtctttc aaag                                            24

<210> SEQ ID NO 10
<211> LENGTH: 25
<212> TYPE: DNA
<213> ORGANISM: homo sapiens
```

-continued

```
<400> SEQUENCE: 10
gtgctcagcc cacgccccgg cgctg                                           25

<210> SEQ ID NO 11
<211> LENGTH: 25
<212> TYPE: DNA
<213> ORGANISM: homo sapiens

<400> SEQUENCE: 11
ccagcatctc cacgaaggca gagtt                                           25

<210> SEQ ID NO 12
<211> LENGTH: 25
<212> TYPE: DNA
<213> ORGANISM: homo sapiens

<400> SEQUENCE: 12
agcttccaac cacgtgtaaa tccta                                           25

<210> SEQ ID NO 13
<211> LENGTH: 25
<212> TYPE: DNA
<213> ORGANISM: homo sapiens

<400> SEQUENCE: 13
gtgacatttt cacggccata gcgaa                                           25

<210> SEQ ID NO 14
<211> LENGTH: 25
<212> TYPE: DNA
<213> ORGANISM: homo sapiens

<400> SEQUENCE: 14
cgaaccaggg cacgtgcaat ggcga                                           25

<210> SEQ ID NO 15
<211> LENGTH: 25
<212> TYPE: DNA
<213> ORGANISM: homo sapiens

<400> SEQUENCE: 15
gcttgtgatc cacggacact cctac                                           25

<210> SEQ ID NO 16
<211> LENGTH: 5
<212> TYPE: PRT
<213> ORGANISM: homo sapiens

<400> SEQUENCE: 16

Leu Lys Lys Glu Pro
1               5

<210> SEQ ID NO 17
<211> LENGTH: 5
<212> TYPE: PRT
<213> ORGANISM: homo sapiens

<400> SEQUENCE: 17

Leu Lys Leu Glu Pro
1               5

<210> SEQ ID NO 18
<211> LENGTH: 7
```

```
<212> TYPE: PRT
<213> ORGANISM: homo sapiens

<400> SEQUENCE: 18

Leu Lys Leu Glu Pro Asn Pro
1               5

<210> SEQ ID NO 19
<211> LENGTH: 4
<212> TYPE: PRT
<213> ORGANISM: homo sapiens

<400> SEQUENCE: 19

Phe Lys Leu Glu
1

<210> SEQ ID NO 20
<211> LENGTH: 4
<212> TYPE: PRT
<213> ORGANISM: homo sapiens

<400> SEQUENCE: 20

Arg Lys Met Glu
1

<210> SEQ ID NO 21
<211> LENGTH: 7
<212> TYPE: PRT
<213> ORGANISM: homo sapiens

<400> SEQUENCE: 21

Arg Lys Met Glu His Asp Gly
1               5

<210> SEQ ID NO 22
<211> LENGTH: 20
<212> TYPE: DNA
<213> ORGANISM: homo sapiens

<400> SEQUENCE: 22
cacagcagcg gcctcgggta                                              20

<210> SEQ ID NO 23
<211> LENGTH: 20
<212> TYPE: DNA
<213> ORGANISM: homo sapiens

<400> SEQUENCE: 23
catgatgacg gtggcttcac                                              20

<210> SEQ ID NO 24
<211> LENGTH: 20
<212> TYPE: DNA
<213> ORGANISM: homo sapiens

<400> SEQUENCE: 24
gtgacctctc tgtgcacacg                                              20

<210> SEQ ID NO 25
<211> LENGTH: 5
<212> TYPE: DNA
<213> ORGANISM: homo sapiens

<400> SEQUENCE: 25
```

-continued

```
rcgtg                                                       5

<210> SEQ ID NO 26
<211> LENGTH: 24
<212> TYPE: DNA
<213> ORGANISM: homo sapiens

<400> SEQUENCE: 26
ctttgaaaga cgtgtctaca taag                                 24

<210> SEQ ID NO 27
<211> LENGTH: 25
<212> TYPE: DNA
<213> ORGANISM: homo sapiens

<400> SEQUENCE: 27
cagcgccggg gcgtgggctg agcac                                25

<210> SEQ ID NO 28
<211> LENGTH: 25
<212> TYPE: DNA
<213> ORGANISM: homo sapiens

<400> SEQUENCE: 28
aactctgcct tcgtggagat gctgg                                25

<210> SEQ ID NO 29
<211> LENGTH: 25
<212> TYPE: DNA
<213> ORGANISM: homo sapiens

<400> SEQUENCE: 29
taggatttac acgtggttgg aagct                                25

<210> SEQ ID NO 30
<211> LENGTH: 25
<212> TYPE: DNA
<213> ORGANISM: homo sapiens

<400> SEQUENCE: 30
ttcgctatgg ccgtgaaaat gtcac                                25

<210> SEQ ID NO 31
<211> LENGTH: 25
<212> TYPE: DNA
<213> ORGANISM: homo sapiens

<400> SEQUENCE: 31
tcgccattgc acgtgccctg gttcg                                25

<210> SEQ ID NO 32
<211> LENGTH: 25
<212> TYPE: DNA
<213> ORGANISM: homo sapiens

<400> SEQUENCE: 32
gtaggagtgt ccgtggatca caagc                                25

<210> SEQ ID NO 33
<211> LENGTH: 26
<212> TYPE: DNA
<213> ORGANISM: homo sapiens

<400> SEQUENCE: 33
```
ttggtgccat ggccgtgggg caagtc                                          26

<210> SEQ ID NO 34
<211> LENGTH: 26
<212> TYPE: DNA
<213> ORGANISM: homo sapiens

<400> SEQUENCE: 34
cacctgggca tcgtgtccca ggagcc                                          26

<210> SEQ ID NO 35
<211> LENGTH: 25
<212> TYPE: DNA
<213> ORGANISM: homo sapiens

<400> SEQUENCE: 35
caggaagaga tcgtgagggc agcaa                                           25

<210> SEQ ID NO 36
<211> LENGTH: 29
<212> TYPE: DNA
<213> ORGANISM: homo sapiens

<400> SEQUENCE: 36
cattgccata gctcgtgccc ttgttagac                                       29

<210> SEQ ID NO 37
<211> LENGTH: 20
<212> TYPE: DNA
<213> ORGANISM: homo sapiens

<400> SEQUENCE: 37
aacggaagcc agaacattcc                                                 20

<210> SEQ ID NO 38
<211> LENGTH: 20
<212> TYPE: DNA
<213> ORGANISM: homo sapiens

<400> SEQUENCE: 38
aggcttcctg tggcaaagag                                                 20

<210> SEQ ID NO 39
<211> LENGTH: 20
<212> TYPE: DNA
<213> ORGANISM: homo sapiens

<400> SEQUENCE: 39
ctcaaagtcg gacagcctca                                                 20

<210> SEQ ID NO 40
<211> LENGTH: 20
<212> TYPE: DNA
<213> ORGANISM: homo sapiens

<400> SEQUENCE: 40
ccctgcagta ggtttctgct                                                 20

<210> SEQ ID NO 41
<211> LENGTH: 24
<212> TYPE: DNA
<213> ORGANISM: homo sapiens

```
<400> SEQUENCE: 41
atgacttcca agctggccgt ggct                                      24

<210> SEQ ID NO 42
<211> LENGTH: 25
<212> TYPE: DNA
<213> ORGANISM: homo sapiens

<400> SEQUENCE: 42
tctcagccct cttcaaaaac ttctc                                     25

<210> SEQ ID NO 43
<211> LENGTH: 21
<212> TYPE: DNA
<213> ORGANISM: homo sapiens

<400> SEQUENCE: 43
cgtcatcatg tctgaccagg a                                         21

<210> SEQ ID NO 44
<211> LENGTH: 21
<212> TYPE: DNA
<213> ORGANISM: homo sapiens

<400> SEQUENCE: 44
cactgaaagt cacagtccag g                                         21

<210> SEQ ID NO 45
<211> LENGTH: 30
<212> TYPE: DNA
<213> ORGANISM: homo sapiens

<400> SEQUENCE: 45
tgacggggtc acccacactg tgcccatcta                                30

<210> SEQ ID NO 46
<211> LENGTH: 30
<212> TYPE: DNA
<213> ORGANISM: homo sapiens

<400> SEQUENCE: 46
ctagaagcat ttgcggtgga cgatggaggg                                30

<210> SEQ ID NO 47
<211> LENGTH: 15
<212> TYPE: DNA
<213> ORGANISM: homo sapiens

<400> SEQUENCE: 47
gccggcgccc tccat                                                15

<210> SEQ ID NO 48
<211> LENGTH: 15
<212> TYPE: DNA
<213> ORGANISM: homo sapiens

<400> SEQUENCE: 48
atggagggcg ccggc                                                15

<210> SEQ ID NO 49
<211> LENGTH: 39
<212> TYPE: DNA
<213> ORGANISM: homo sapiens
```

```
<400> SEQUENCE: 49
aggaccagcg ccggggccat ggctgagcac agccgcttc                    39

<210> SEQ ID NO 50
<211> LENGTH: 29
<212> TYPE: DNA
<213> ORGANISM: homo sapiens

<400> SEQUENCE: 50
aggaacagcg ccgggggctg agcacagcc                              29

<210> SEQ ID NO 51
<211> LENGTH: 23
<212> TYPE: DNA
<213> ORGANISM: homo sapiens

<400> SEQUENCE: 51
tttgaaagac gtgtctacat aag                                    23

<210> SEQ ID NO 52
<211> LENGTH: 22
<212> TYPE: DNA
<213> ORGANISM: homo sapiens

<400> SEQUENCE: 52
ttgaaagacg tgtctacata ag                                     22

<210> SEQ ID NO 53
<211> LENGTH: 21
<212> TYPE: DNA
<213> ORGANISM: homo sapiens

<400> SEQUENCE: 53
tgaaagacgt gtctacataa g                                      21

<210> SEQ ID NO 54
<211> LENGTH: 21
<212> TYPE: DNA
<213> ORGANISM: homo sapiens

<400> SEQUENCE: 54
tgaaagacgt gtctacataa g                                      21

<210> SEQ ID NO 55
<211> LENGTH: 23
<212> TYPE: DNA
<213> ORGANISM: homo sapiens

<400> SEQUENCE: 55
ctttgaaaga cgtgtctaca taa                                    23

<210> SEQ ID NO 56
<211> LENGTH: 22
<212> TYPE: DNA
<213> ORGANISM: homo sapiens

<400> SEQUENCE: 56
ctttgaaaga cgtgtctaca ta                                     22

<210> SEQ ID NO 57
<211> LENGTH: 21
<212> TYPE: DNA
```

<210> SEQ ID NO 58
<211> LENGTH: 20
<212> TYPE: DNA
<213> ORGANISM: homo sapiens

<400> SEQUENCE: 58
ctttgaaaga cgtgtctaca                                              20

<210> SEQ ID NO 59
<211> LENGTH: 2818
<212> TYPE: DNA
<213> ORGANISM: homo sapiens

<400> SEQUENCE: 59

| | | | | | |
|---|---|---|---|---|---|
| cctgactgcg | cggggcgctc | gggacctgcg | cgcacctcgg | accttcacca | cccgcccggg | 60 |
| ccgcggggag | cggacgaggg | ccacagcccc | cacccgcca | gggagcccag | gtgctcggcg | 120 |
| tctgaacgtc | tcaaagggcc | acagcgacaa | tgacagctga | caaggagaag | aaaaggagta | 180 |
| gctcggagag | gaggaaggag | aagtcccggg | atgctgcgcg | gtgccggcgg | agcaaggaga | 240 |
| cggaggtgtt | ctatgagctg | gcccatgagc | tgcctctgcc | ccacagtgtg | agctcccatc | 300 |
| tggacaaggc | ctccatcatg | cgactggaaa | tcagcttcct | gcgaacacac | aagctccctct | 360 |
| cctcagtttg | ctctgaaaac | gagtccgaag | ccgaagctga | ccagcagatg | gacaacttgt | 420 |
| acctgaaagc | cttggagggt | ttcattgccg | tggtgaccca | agatggcgac | atgatctttc | 480 |
| tgtcagaaaa | catcagcaag | ttcatgggac | ttacacaggt | ggagctaaca | ggacatagta | 540 |
| tctttgactt | cactcatccc | tgcgaccatg | aggagattcg | tgagaacctg | agtctcaaaa | 600 |
| atggctctgg | ttttgggaaa | aaagcaaag | acatgtccac | agagcgggac | ttcttcatga | 660 |
| ggatgaagtg | cacggtcacc | aacagaggcc | gtactgtcaa | cctcaagtca | gccacctgga | 720 |
| aggtcttgca | ctgcacgggc | caggtgaaag | tctacaacaa | ctgccctcct | cacaatagtc | 780 |
| tgtgtggcta | caaggagccc | ctgctgtcct | gcctcatcat | catgtgtgaa | ccaatccagc | 840 |
| acccatccca | catggacatc | cccctggata | gcaagacctt | cctgagccgc | cacagcatgg | 900 |
| acatgaagtt | cacctactgt | gatgacagaa | tcacagaact | gattggttac | caccctgagg | 960 |
| agctgcttgg | ccgctcagcc | tatgaattct | accatgcgct | agactccgag | aacatgacca | 1020 |
| agagtcacca | gaacttgtgc | accaagggtc | aggtagtaag | tggccagtac | cggatgctcg | 1080 |
| caaagcatgg | gggctacgtg | tggctggaga | cccagggac | ggtcatctac | aaccctcgca | 1140 |
| acctgcagcc | ccagtgcatc | atgtgtgtca | actacgtcct | gagtgagatt | gagaagaatg | 1200 |
| acgtggtgtt | ctccatggac | cagactgaat | ccctgttcaa | gccccacctg | atggccatga | 1260 |
| acagcatctt | tgatagcagt | ggcaagggggg | ctgtgtctga | aagagtaac | ttcctattca | 1320 |
| ccaagctaaa | ggaggagccc | gaggagctgg | cccagctggc | tcccaccccca | ggagacgcca | 1380 |
| tcatctctct | ggatttcggg | aatcagaact | cgaggagtc | ctcagcctat | ggcaaggcca | 1440 |
| tcctgccccc | gagccagcca | tgggccacgg | agttgaggag | ccacagcacc | cagagcgagg | 1500 |
| ctgggagcct | gctgccttc | accgtgcccc | aggcagctgc | cccgggcagc | accaccccca | 1560 |
| gtgccaccag | cagcagcagc | agctgctcca | cgcccaatag | ccctgaagac | tattacacat | 1620 |
| ctttggataa | cgacctgaag | attgaagtga | ttgagaagct | cttcgccatg | gacacagagg | 1680 |

```
ccaaggacca atgcagtacc cagacggatt tcaatgagct ggacttggag acactggcac   1740
cctatatccc catggacggg aagacttcc  agctaagccc catctgcccc gaggagcggc   1800
tcttggcgga aacccacag  tccaccccc  agcactgctt cagtgccatg acaaacatct   1860
tccagccact ggcccctgta gccccgcaca gtcccttcct cctggacaag tttcagcagc   1920
agctggagag caagaagaca gagcccgagc accggcccat gtcctccatc ttctttgatg   1980
ccggaagcaa agcatccctg ccaccgtgct gtggccaggc cagcacccct ctctcttcca   2040
tggggggcag atccaatacc cagtggcccc cagatccacc attacatttt gggcccacaa   2100
agtgggccgt cggggatcag cgcacagagt tcttgggagc agcgccgttg gggcccctg    2160 tctctccacc ccatgtctcc accttcaaga caaggtctgc aaagggtttt ggggctcgag   2220
gcccagacgt gctgagtccg gccatggtag ccctctccaa caagctgaag ctgaagcgac   2280
agctggagta tgaagagcaa gccttccagg acctgagcgg gggggaccca cctggtggca   2340
gcacctcaca tttgatgtgg aaacggatga agaacctcag gggtgggagc tgccctttga   2400
tgccggacaa gccactgagc gcaaatgtac ccaatgataa gttcacccaa aaccccatga   2460
ggggcctggg ccatcccctg agacatctgc cgctgccaca gcctccatct gccatcagtc   2520
ccggggagaa cagcaagagc aggttccccc cacagtgcta cgccacccag taccaggact   2580
acagcctgtc gtcagcccac aaggtgtcag gcatggcaag ccggctgctc gggccctcat   2640
ttgagtccta cctgctgccc gaactgacca gatatgactg tgaggtgaac gtgcccgtgc   2700
tgggaagctc cacgctcctg caaggagggg acctcctcag agccctggac caggccacct   2760
gagccaggcc ttctacctgg gcagcacctc tgccgacgcc gtcccaccag cttcaccc    2818

<210> SEQ ID NO 60
<211> LENGTH: 870
<212> TYPE: PRT
<213> ORGANISM: homo sapiens

<400> SEQUENCE: 60

Met Thr Ala Asp Lys Glu Lys Lys Arg Ser Ser Glu Arg Arg Lys
1               5                   10                  15

Glu Lys Ser Arg Asp Ala Ala Arg Cys Arg Arg Ser Lys Glu Thr Glu
                20                  25                  30

Val Phe Tyr Glu Leu Ala His Glu Leu Pro Leu Pro His Ser Val Ser
            35                  40                  45

Ser His Leu Asp Lys Ala Ser Ile Met Arg Leu Glu Ile Ser Phe Leu
        50                  55                  60

Arg Thr His Lys Leu Leu Ser Ser Val Cys Ser Glu Asn Glu Ser Glu
65                  70                  75                  80

Ala Glu Ala Asp Gln Gln Met Asp Asn Leu Tyr Leu Lys Ala Leu Glu
                85                  90                  95

Gly Phe Ile Ala Val Val Thr Gln Asp Gly Asp Met Ile Phe Leu Ser
            100                 105                 110

Glu Asn Ile Ser Lys Phe Met Gly Leu Thr Gln Val Glu Leu Thr Gly
        115                 120                 125

His Ser Ile Phe Asp Phe Thr His Pro Cys Asp His Glu Glu Ile Arg
        130                 135                 140

Glu Asn Leu Ser Leu Lys Asn Gly Ser Gly Phe Gly Lys Lys Ser Lys
145                 150                 155                 160

Asp Met Ser Thr Glu Arg Asp Phe Phe Met Arg Met Lys Cys Thr Val
                165                 170                 175
```

```
Thr Asn Arg Gly Arg Thr Val Asn Leu Lys Ser Ala Thr Trp Lys Val
            180                 185                 190

Leu His Cys Thr Gly Gln Val Lys Val Tyr Asn Asn Cys Pro Pro His
        195                 200                 205

Asn Ser Leu Cys Gly Tyr Lys Glu Pro Leu Leu Ser Cys Leu Ile Ile
    210                 215                 220

Met Cys Glu Pro Ile Gln His Pro Ser His Met Asp Ile Pro Leu Asp
225                 230                 235                 240

Ser Lys Thr Phe Leu Ser Arg His Ser Met Asp Met Lys Phe Thr Tyr
                245                 250                 255

Cys Asp Asp Arg Ile Thr Glu Leu Ile Gly Tyr His Pro Glu Glu Leu
            260                 265                 270

Leu Gly Arg Ser Ala Tyr Glu Phe Tyr His Ala Leu Asp Ser Glu Asn
        275                 280                 285

Met Thr Lys Ser His Gln Asn Leu Cys Thr Lys Gly Gln Val Val Ser
    290                 295                 300

Gly Gln Tyr Arg Met Leu Ala Lys His Gly Gly Tyr Val Trp Leu Glu
305                 310                 315                 320

Thr Gln Gly Thr Val Ile Tyr Asn Pro Arg Asn Leu Gln Pro Gln Cys
                325                 330                 335

Ile Met Cys Val Asn Tyr Val Leu Ser Glu Ile Glu Lys Asn Asp Val
            340                 345                 350

Val Phe Ser Met Asp Gln Thr Glu Ser Leu Phe Lys Pro His Leu Met
        355                 360                 365

Ala Met Asn Ser Ile Phe Asp Ser Ser Gly Lys Gly Ala Val Ser Glu
    370                 375                 380

Lys Ser Asn Phe Leu Phe Thr Lys Leu Lys Glu Glu Pro Glu Glu Leu
385                 390                 395                 400

Ala Gln Leu Ala Pro Thr Pro Gly Asp Ala Ile Ile Ser Leu Asp Phe
                405                 410                 415

Gly Asn Gln Asn Phe Glu Glu Ser Ser Ala Tyr Gly Lys Ala Ile Leu
            420                 425                 430

Pro Pro Ser Gln Pro Trp Ala Thr Glu Leu Arg Ser His Ser Thr Gln
        435                 440                 445

Ser Glu Ala Gly Ser Leu Pro Ala Phe Thr Val Pro Gln Ala Ala Ala
    450                 455                 460

Pro Gly Ser Thr Thr Pro Ser Ala Thr Ser Ser Ser Ser Cys Ser
465                 470                 475                 480

Thr Pro Asn Ser Pro Glu Asp Tyr Tyr Thr Ser Leu Asp Asn Asp Leu
                485                 490                 495

Lys Ile Glu Val Ile Glu Lys Leu Phe Ala Met Asp Thr Glu Ala Lys
            500                 505                 510

Asp Gln Cys Ser Thr Gln Thr Asp Phe Asn Glu Leu Asp Leu Glu Thr
        515                 520                 525

Leu Ala Pro Tyr Ile Pro Met Asp Gly Glu Asp Phe Gln Leu Ser Pro
    530                 535                 540

Ile Cys Pro Glu Glu Arg Leu Leu Ala Glu Asn Pro Gln Ser Thr Pro
545                 550                 555                 560

Gln His Cys Phe Ser Ala Met Thr Asn Ile Phe Gln Pro Leu Ala Pro
                565                 570                 575

Val Ala Pro His Ser Pro Phe Leu Leu Asp Lys Phe Gln Gln Gln Leu
            580                 585                 590
```

-continued

| | | | | | | | | | | | | | |
|---|---|---|---|---|---|---|---|---|---|---|---|---|---|
| Glu | Ser | Lys | Lys | Thr | Glu | Pro | Glu | His | Arg | Pro | Met | Ser | Ser | Ile | Phe |
| | | | 595 | | | | | 600 | | | | | 605 | | |
| Phe | Asp | Ala | Gly | Ser | Lys | Ala | Ser | Leu | Pro | Pro | Cys | Cys | Gly | Gln | Ala |
| | 610 | | | | | 615 | | | | | 620 | | | | |
| Ser | Thr | Pro | Leu | Ser | Ser | Met | Gly | Gly | Arg | Ser | Asn | Thr | Gln | Trp | Pro |
| 625 | | | | | 630 | | | | | 635 | | | | | 640 |
| Pro | Asp | Pro | Pro | Leu | His | Phe | Gly | Pro | Thr | Lys | Trp | Ala | Val | Gly | Asp |
| | | | | 645 | | | | | 650 | | | | | 655 | |
| Gln | Arg | Thr | Glu | Phe | Leu | Gly | Ala | Ala | Pro | Leu | Gly | Pro | Pro | Val | Ser |
| | | | 660 | | | | | 665 | | | | | 670 | | |
| Pro | Pro | His | Val | Ser | Thr | Phe | Lys | Thr | Arg | Ser | Ala | Lys | Gly | Phe | Gly |
| | | 675 | | | | | 680 | | | | | 685 | | | |
| Ala | Arg | Gly | Pro | Asp | Val | Leu | Ser | Pro | Ala | Met | Val | Ala | Leu | Ser | Asn |
| | 690 | | | | | 695 | | | | | 700 | | | | |
| Lys | Leu | Lys | Leu | Lys | Arg | Gln | Leu | Glu | Tyr | Glu | Gln | Ala | Phe | Gln |
| 705 | | | | | 710 | | | | | 715 | | | | | 720 |
| Asp | Leu | Ser | Gly | Gly | Asp | Pro | Pro | Gly | Gly | Ser | Thr | Ser | His | Leu | Met |
| | | | | 725 | | | | | 730 | | | | | 735 | |
| Trp | Lys | Arg | Met | Lys | Asn | Leu | Arg | Gly | Gly | Ser | Cys | Pro | Leu | Met | Pro |
| | | | 740 | | | | | 745 | | | | | 750 | | |
| Asp | Lys | Pro | Leu | Ser | Ala | Asn | Val | Pro | Asn | Asp | Lys | Phe | Thr | Gln | Asn |
| | | 755 | | | | | 760 | | | | | 765 | | | |
| Pro | Met | Arg | Gly | Leu | Gly | His | Pro | Leu | Arg | His | Leu | Pro | Leu | Pro | Gln |
| | 770 | | | | | 775 | | | | | 780 | | | | |
| Pro | Pro | Ser | Ala | Ile | Ser | Pro | Gly | Glu | Asn | Ser | Lys | Ser | Arg | Phe | Pro |
| 785 | | | | | 790 | | | | | 795 | | | | | 800 |
| Pro | Gln | Cys | Tyr | Ala | Thr | Gln | Tyr | Gln | Asp | Tyr | Ser | Leu | Ser | Ser | Ala |
| | | | | 805 | | | | | 810 | | | | | 815 | |
| His | Lys | Val | Ser | Gly | Met | Ala | Ser | Arg | Leu | Leu | Gly | Pro | Ser | Phe | Glu |
| | | | 820 | | | | | 825 | | | | | 830 | | |
| Ser | Tyr | Leu | Leu | Pro | Glu | Leu | Thr | Arg | Tyr | Asp | Cys | Glu | Val | Asn | Val |
| | | 835 | | | | | 840 | | | | | 845 | | | |
| Pro | Val | Leu | Gly | Ser | Ser | Thr | Leu | Leu | Gln | Gly | Gly | Asp | Leu | Leu | Arg |
| | 850 | | | | | 855 | | | | | 860 | | | | |
| Ala | Leu | Asp | Gln | Ala | Thr |
| 865 | | | | | 870 |

<210> SEQ ID NO 61
<211> LENGTH: 2004
<212> TYPE: DNA
<213> ORGANISM: homo sapiens

<400> SEQUENCE: 61

```
atggactggc aagaccacag gtcgaccacg gagctgcgca aggaaaagtc ccgggatgcg      60
gcccgcagcc ggcgcagcca ggagaccgag gtgctgtacc agctggctca cacgctgccc     120
ttcgcccgcg gcgtcagcgc ccacctggac aaggcctcta tcatgcgcct caccatcagc     180
tacctgcgca tgcaccgcct ctgcgccgca ggggagtgga accaggtggg agcagggggga    240
gaaccactgg atgcctgcta cctgaaggcc ctggagggct tcgtcatggt gctcaccgcc     300
gagggagaca tggcttacct gtcggagaat gtcagcaaac acctgggcct cagtcagctg     360
gagctcattg acacagcat ctttgatttc atccaccct gtgaccaaga ggagcttcag       420
gacgccctga cccccagca gacctgtcc aggaggaagg tggaggcccc cacgagcgg        480
tgcttctcct tgcgcatgaa gagtacgctc accagccgcg ggcgcaccct caacctcaag     540
```

-continued

```
gcggccacct ggaaggtgct gaactgctct ggacatatga gggcctacaa gccacctgcg      600
cagacttctc cagctgggag ccctgactca gagcccccgc tgcagtgcct ggtgctcatc      660
tgcgaagcca tcccccaccc aggcagcctg agcccccac tgggccgagg ggccttcctc       720
agccgccaca gcctggacat gaagttcacc tactgtgacg acaggattgc agaagtggct      780
ggctatagtc ccgatgacct gatcggctgt tccgcctacg agtacatcca cgcgctggac      840
tccgacgcgg tcagcaagag catccacacc ttgctgagca agggccaggc agtaacaggg      900
cagtatcgct tcctggcccg gagtggtggc tacctgtgga cccagaccca ggccacagtg      960
gtgtcagggg acgggcccc ccagtcggag agtatcgtct gtgtccattt tttaatcagc       1020
caggtggaag agaccggagt ggtgctgtcc ctggagcaaa cggagcaaca ctctcgcaga      1080
cccattcagc ggggcgcccc ctctcagaag gacacccta accctgggga cagccttgac       1140 accctggcc cccggatcct tgccttcctg cacccgcctt ccctgagcga ggctgccctg       1200
gccgctgacc cccgccgttt ctgcagccct gacctccgtc gcctcctggg acccatcctg      1260 gatgggctt cagtagcagc cactcccagc acccgctgg ccacacggca ccccaaagt        1320 cctctttcgg ctgatctccc agatgaacta cctgtgggca ccgagaatgt gcacagactc      1380
ttcacctccg ggaaagacac tgaggcagtg gagacagatt tagatatagc tcaggatgct     1440
gatgctctgg atttggagat gctggccccc tacatctcca tggatgatga cttccagctc     1500
aacgccagcg agcagctacc cagggcctac cacagacctc tggggctgt ccccggccc       1560 cgtgctcgga gcttccatgg cctgtcacct ccagcccttg agcctccct gctaccccgc       1620 tgggggagtg accccggct gagctgctcc agcccttcca gagggaccc ctcagcatcc       1680 tctcccatgg ctggggctcg gaagaggacc ctggcccaga gctcagagga cgaggacgag      1740
ggagtggagc tgctgggagt gagacctccc aaaaggtccc ccagcccaga acacgaaaac      1800
tttctgctct ttcctctcag cctgagtttc cttctgacag gaggaccagc cccagggagc      1860
ctgcaggacc ccagcacccc actcctgaac ctgaatgagc ccctgggcct gggcccctca      1920
ctgctctctc cgtactcaga cgaggacact acccagcccg ggggccccctt ccagccaagg     1980 gcaggctcag cccaggctga ctga                                            2004
```

<210> SEQ ID NO 62
<211> LENGTH: 667
<212> TYPE: PRT
<213> ORGANISM: homo sapiens

<400> SEQUENCE: 62

Met Asp Trp Gln Asp His Arg Ser Thr Thr Glu Leu Arg Lys Glu Lys
1               5                   10                  15

Ser Arg Asp Ala Ala Arg Ser Arg Arg Ser Gln Glu Thr Glu Val Leu
                20                  25                  30

Tyr Gln Leu Ala His Thr Leu Pro Phe Ala Arg Gly Val Ser Ala His
            35                  40                  45

Leu Asp Lys Ala Ser Ile Met Arg Leu Thr Ile Ser Tyr Leu Arg Met
        50                  55                  60

His Arg Leu Cys Ala Ala Gly Glu Trp Asn Gln Val Gly Ala Gly Gly
65                  70                  75                  80

Glu Pro Leu Asp Ala Cys Tyr Leu Lys Ala Leu Glu Gly Phe Val Met
                85                  90                  95

Val Leu Thr Ala Glu Gly Asp Met Ala Tyr Leu Ser Glu Asn Val Ser
            100                 105                 110

```
Lys His Leu Gly Leu Ser Gln Leu Glu Leu Ile Gly His Ser Ile Phe
        115                 120                 125

Asp Phe Ile His Pro Cys Asp Gln Glu Glu Leu Gln Asp Ala Leu Thr
    130                 135                 140

Pro Gln Gln Thr Leu Ser Arg Arg Lys Val Glu Ala Pro Thr Glu Arg
145                 150                 155                 160

Cys Phe Ser Leu Arg Met Lys Ser Thr Leu Thr Ser Arg Gly Arg Thr
                165                 170                 175

Leu Asn Leu Lys Ala Ala Thr Trp Lys Val Leu Asn Cys Ser Gly His
            180                 185                 190

Met Arg Ala Tyr Lys Pro Pro Ala Gln Thr Ser Pro Ala Gly Ser Pro
        195                 200                 205

Asp Ser Glu Pro Pro Leu Gln Cys Leu Val Leu Ile Cys Glu Ala Ile
    210                 215                 220

Pro His Pro Gly Ser Leu Glu Pro Pro Leu Gly Arg Gly Ala Phe Leu
225                 230                 235                 240

Ser Arg His Ser Leu Asp Met Lys Phe Thr Tyr Cys Asp Asp Arg Ile
                245                 250                 255

Ala Glu Val Ala Gly Tyr Ser Pro Asp Asp Leu Ile Gly Cys Ser Ala
            260                 265                 270

Tyr Glu Tyr Ile His Ala Leu Asp Ser Asp Ala Val Ser Lys Ser Ile
        275                 280                 285

His Thr Leu Leu Ser Lys Gly Gln Ala Val Thr Gly Gln Tyr Arg Phe
    290                 295                 300

Leu Ala Arg Ser Gly Gly Tyr Leu Trp Thr Gln Thr Gln Ala Thr Val
305                 310                 315                 320

Val Ser Gly Gly Arg Gly Pro Gln Ser Glu Ser Ile Val Cys Val His
                325                 330                 335

Phe Leu Ile Ser Gln Val Glu Glu Thr Gly Val Val Leu Ser Leu Glu
            340                 345                 350

Gln Thr Glu Gln His Ser Arg Arg Pro Ile Gln Arg Gly Ala Pro Ser
        355                 360                 365

Gln Lys Asp Thr Pro Asn Pro Gly Asp Ser Leu Asp Thr Pro Gly Pro
    370                 375                 380

Arg Ile Leu Ala Phe Leu His Pro Pro Ser Leu Ser Glu Ala Ala Leu
385                 390                 395                 400

Ala Ala Asp Pro Arg Arg Phe Cys Ser Pro Asp Leu Arg Arg Leu Leu
                405                 410                 415

Gly Pro Ile Leu Asp Gly Ala Ser Val Ala Ala Thr Pro Ser Thr Pro
            420                 425                 430

Leu Ala Thr Arg His Pro Gln Ser Pro Leu Ser Ala Asp Leu Pro Asp
        435                 440                 445

Glu Leu Pro Val Gly Thr Glu Asn Val His Arg Leu Phe Thr Ser Gly
    450                 455                 460

Lys Asp Thr Glu Ala Val Glu Thr Asp Leu Asp Ile Ala Gln Asp Ala
465                 470                 475                 480

Asp Ala Leu Asp Leu Glu Met Leu Ala Pro Tyr Ile Ser Met Asp Asp
                485                 490                 495

Asp Phe Gln Leu Asn Ala Ser Glu Gln Leu Pro Arg Ala Tyr His Arg
            500                 505                 510

Pro Leu Gly Ala Val Pro Arg Pro Arg Ala Arg Ser Phe His Gly Leu
        515                 520                 525
```

-continued

Ser Pro Pro Ala Leu Glu Pro Ser Leu Leu Pro Arg Trp Gly Ser Asp
    530                 535                 540

Pro Arg Leu Ser Cys Ser Ser Pro Ser Arg Gly Asp Pro Ser Ala Ser
545                 550                 555                 560

Ser Pro Met Ala Gly Ala Arg Lys Arg Thr Leu Ala Gln Ser Ser Glu
                565                 570                 575

Asp Glu Asp Glu Gly Val Glu Leu Leu Gly Val Arg Pro Pro Lys Arg
            580                 585                 590

Ser Pro Ser Pro Glu His Glu Asn Phe Leu Leu Phe Pro Leu Ser Leu
    595                 600                 605

Ser Phe Leu Leu Thr Gly Gly Pro Ala Pro Gly Ser Leu Gln Asp Pro
    610                 615                 620

Ser Thr Pro Leu Leu Asn Leu Asn Glu Pro Leu Gly Leu Gly Pro Ser
625                 630                 635                 640

Leu Leu Ser Pro Tyr Ser Asp Glu Asp Thr Thr Gln Pro Gly Gly Pro
                645                 650                 655

Phe Gln Pro Arg Ala Gly Ser Ala Gln Ala Asp
            660                 665

<210> SEQ ID NO 63
<211> LENGTH: 12
<212> TYPE: PRT
<213> ORGANISM: homo sapiens

<400> SEQUENCE: 63

Tyr Gly Arg Lys Lys Arg Arg Gln Arg Arg Gly
1               5                   10

<210> SEQ ID NO 64
<211> LENGTH: 11
<212> TYPE: PRT
<213> ORGANISM: homo sapiens

<400> SEQUENCE: 64

Ala Gln Arg Lys Arg Lys Met Glu His Asp Gly
1               5                   10

<210> SEQ ID NO 65
<211> LENGTH: 11
<212> TYPE: PRT
<213> ORGANISM: homo sapiens

<400> SEQUENCE: 65

Phe Asp Lys Leu Lys Lys Glu Pro Asp Ala Leu
1               5                   10

<210> SEQ ID NO 66
<211> LENGTH: 12
<212> TYPE: PRT
<213> ORGANISM: homo sapiens

<400> SEQUENCE: 66

Glu Val Ala Leu Lys Leu Glu Pro Asn Pro Glu Ser
1               5                   10

<210> SEQ ID NO 67
<211> LENGTH: 12

-continued

```
<212> TYPE: PRT
<213> ORGANISM: homo sapiens

<400> SEQUENCE: 67

Asp Met Val Asn Glu Phe Lys Leu Glu Leu Val Glu
1               5                   10
```

COMPOSITIONS AND METHODS FOR TREATING HEMATOLOGIC MALIGNANCIES AND MULTIPLE DRUG RESISTANCE

RELATED APPLICATIONS

This application claims priority under 35 U.S.C. § 119 to U.S. provisional application Ser. No. 60/243,542, filed Oct. 26, 2000.

GOVERNMENT RIGHTS

This invention was funded in part under National Institute of Health Grant No. DK50189. The government may retain certain rights in the invention.

FIELD OF THE INVENTION

The inventions relate to compositions and methods for treating certain cancers and/or reducing multidrug resistance that may be associated with such cancers. More particularly, the invention relates to methods for modulating the expression of HIF-1 and/or MDR.

BACKGROUND OF THE INVENTION

The development of simultaneous resistance to multiple structurally unrelated drugs is a major impediment to cancer chemotherapy. (Roepe, Curr. Pharm. Des. 6:241, 2000). Multidrug resistance is associated with specific DNA sequences termed the multidrug resistance locus (mdr1) (Roepe, Curr. Pharm. Des. 6:241, 2000). Increased expression and amplification of mdr1 sequences have been reported in numerous multidrug-resistant sublines of human leukemia and ovarian carcinoma cells. Overexpression of the mdr1 gene product (P-glycoprotein) reportedly is a feature of mammalian cells displaying resistance to multiple anticancer drugs and has been postulated to mediate resistance. Multidrug resistance correlates with amplification of two related DNA sequences, designated mdr1 and mdr2 (mdr2 has been referred to by others as mdr3). These sequences were isolated through homology with the Chinese hamster mdr gene. mdr1 encodes a 4.5-kb mRNA and reportedly was amplified or overexpressed in all multidrug-resistant human cell lines analyzed. (Hoffmeyer, S., et al., Proc. Natl. Acad. Sci. USA 97:3473).

The mdr1 gene product P-glycoprotein extrudes a variety of drugs across the plasma membrane. The homologous mdr3 P-glycoprotein is required for phosphatidylcholine secretion into bile. By stable transfection of epithelial cells, mdr1 and mdr3 were localized in the apical membrane. The mdr1 gene product (P-glycoprotein) is the apical membrane protein responsible for the renal secretion of digoxin. This agent has a low therapeutic index and a relatively large and diverse group of coadministered drugs are reported to interact with digoxin, for example, quinidine, verapamil, amiodarone, spironolactone, and cyclosporin, frequently leading to its toxic accumulation (Ueda, et al., Proc. Nat. Acad. Sci. 84:3004–3008, 1987). Since digoxin is a prototype for endogenous digitalis-like glycosides, endogenous digitalis-like glycosides may be the natural substrates for P-glycoprotein. (de Lannoy, I. A. M., et al., Biochem. Biophys. Res. Commun. 189:551–557, 1992).

Increased levels of P-glycoprotein reportedly occur in some osteosarcomas. Baldini et al. (Baldini, et al., New Eng. J. Med. 333:1380–1385, 1995) investigated the relationship between P-glycoprotein status and outcome in 92 patients with high-grade osteosarcoma of the extremities who were treated with surgery and chemotherapy. The presence of increased levels of P-glycoprotein in the osteosarcoma reportedly were significantly associated with a decreased probability of remaining event-free after diagnosis. In a multivariate analysis, P-glycoprotein status and the extent of tumor necrosis after preoperative chemotherapy were independent predictors of clinical outcome. HIV-1 protease inhibitors are potent agents in the therapy of HIV-1 infection. However, limited oral absorption and variable tissue distribution complicate their use. Kim et al. (Kim, et al., J. Clin. Invest. 101:289–294, 1998) reported that P-glycoprotein-1 is involved in the transport of three of these protease inhibitors in vitro. After oral administration, plasma concentrations were elevated 2- to 5-fold in mdr1 α –/– mice carrying the disrupted mdr1 α gene, and with intravenous administration, brain concentrations were elevated 7- to 36-fold. The literature also suggests that P-glycoprotein limits the oral bioavailability and penetration of these agents into the brain (Schinkel, et al., Cell 77:491–502, 1994).

Human solid tumors are considerably less well oxygenated than normal tissues (Brown, Mol. Med. Today, 6:157, 2000). This leads resistance to radiotherapy and anticancer chemotherapy, as well as predisposing to increased tumor metastases, the mechanism(s) of which are not known at present. The microenvironment of rapidly growing tumors is associated with increased energy demand and diminished vascular supply, resulting in concentric areas of cellular hypoxia (Brown, Mol. Med. Today, 6:157, 2000). A number of hypoxia-responsive genes have been associated with growing solid tumors.

In view of the foregoing, a need exists to better understand the mechanism underlying multidrug resistance and cancer genesis and to develop targeted therapeutic agents for treating these and other disorders.

SUMMARY OF THE INVENTION

The invention is based, in part, on the discovery that the multidrug resistance (mdr1) gene product P-glycoprotein (MDR) (SEQ ID NO: 2), a 170-180 kD transmembrane protein associated with tumor resistance to chemotherapeutics, is induced by hypoxia. We have used this information to identify transcriptional elements in the mdr1 gene that are associated with hypoxia inducibility and to develop binding molecules to mdr1 that selectively inhibit mdr1 gene expression that is mediated by hypoxia. Thus, the invention provides antisense molecules that selectively bind to a hypoxia responsive element (HRE) in the mdr1 gene (mdr1-HRE) and, thereby, inhibit transcription of the mdr1 gene.

Prior to this discovery, it was not known that hypoxic conditions induced the expression of the mdr1 gene (SEQ ID NO: 1). Accordingly, the invention provides compositions and methods for selectively modulating mdr1 gene expression, for example, to treat a condition such as a cancer that is associated with multidrug resistance. Thus, the antisense molecule compositions of the invention are useful for treating multidrug resistance associated with various cancers, including those presenting solid tumors and those which do not present solid tumors (hematologic malignancies).

This invention is based, in part, on the discovery of the above-noted nexus between hypoxia and multidrug resistance and the knowledge that cancers which are not associated with solid tumors (e.g., hematologic malignancies such as leukemia) also reportedly exhibit multidrug resistance. In view of this discovery, the invention provides compositions and methods for treating hematologic malignancies. Such compositions include agents which inhibit hypoxia inducible factor-1 (HIF-1) expression, e.g., by blocking hif-1 gene expression or the activity of the hif-1 gene product. Such agents collectively are referred to herein as "HIF-1 binding molecules". These agents can be administered to treat hematologic malignancies alone or in combination with other therapeutic agents, such as the above-noted mdr1 antisense molecules of the invention.

As used herein, "HIF-1 expression" is defined as HIF-1 mRNA expression or HIF-1 polypeptide expression; "mdr1 expression" is defined as mdr1 mRNA expression or MDR polypeptide expression. Various methods can be used to measure expression. The preferred embodiments of the invention utilize PCR and Northern blotting for measuring mRNA expression, and monoclonal or polyclonal HIF-1 antisera as reagents for measuring HIF-1 polypeptide expression (or antibodies to MDR for measuring MDR polypeptide expression). In certain embodiments, a test sample may be a biopsy sample or a biological fluid such as blood. The method is useful, for example, for assessing the efficacy of treatment with the HIF-1 binding molecules (e.g. antisense molecules) and/or the mdr1-HRE binding molecules (e.g. antisense molecules) of the invention.

According to a first aspect of the invention, a method for treating a subject having or at risk of developing a hematologic malignancy is provided. The method involves administering to a subject in need of such treatment and free of indications otherwise calling for treatment with a HIF-1 binding molecule, a HIF-1 binding molecule in an amount effective to treat the hematologic malignancy.

According to certain embodiments of this aspect of the invention, the subject is a mammal, preferably a human. The subject may be undergoing chemotherapy, radiation therapy or a combination of chemotherapy and radiation therapy, about to undergo chemotherapy, radiation therapy or a combination of chemotherapy and radiation therapy, or has recently undergone chemotherapy, radiation therapy, or a combination of chemotherapy and radiation therapy. Optionally, the subject may be presenting symptoms of multidrug resistance.

In some embodiments, the subject has a hematologic maligancy. As used herein, hematologic malignancy is a term of art which refers to a lymphoid disorder or a myeloid disorder.

Lymphoid disorders include acute lymphocytic leukemia and chronic lymphoproliferative disorders (e.g., lymphoma, myeloma, and chronic lymphoid leukemias). Lymphomas include hodgkin's disease and non-hodgkin's lymphoma. Chronic lymphoid leukemias include T cell chronic lymphoid leukemias and B cell chronic lymphoid leukemias.

Myeloid disorders include chronic myeloid disorders and acute myeloid leukemia. Chronic myeloid disorders include chronic myeloproliferative disorders and myelodysplastic syndrome. Chronic myeloproliferative disorders include angiogenic myeloid metaplasia, essential thrombocythemia, chronic myelogenous leukemia, polycythemia vera, and atypical myeloproliferative disorders. Atypical myeloproliferative disorders include atypical CML, chronic neutrophilic leukemia, mast cell disease, and chronic eosinophilic leukemia.

The HIF-1 binding molecule inhibits HIF-1 expression at the transcriptional, translational, or post-translational level. Thus, HIF-1 binding molecules inhibit the ability of the HIF-1 polypeptide to bind to a HRE and induce transcription of the nucleic acid which contains the HRE (which, typically is located in the promoter region of a target gene sequence). Exemplary HIF-1 binding molecules which inhibit transcription of hif-1 gene include antisense to hif-1. Exemplary HIF-1 binding molecules also include binding peptides such as antibodies or antibody fragments which selectively bind to a HIF-1 polypeptide and, thereby, inhibit binding of the HIF-1 to the HRE (See, e.g., U.S. Pat. No. 6,020,462, issued to Semenza). Exemplary HIF-1 binding molecules which selectively bind to a HIF-1 polypeptide and inhibit binding of HIF to the HRE include cell permeant polypeptides.

In certain embodiments of this aspect of the invention, the HIF-1 binding molecule is administered in conjunction with an additional agent(s): (a) for treating or preventing the hematologic malignancy and/or (b) for treating or preventing multidrug resistance. In some embodiments, the agent for treating or preventing multidrug resistance is an mdr1-HRE binding molecule that selectively binds to the HRE in the mdr1 gene and, thereby, inhibits mdr1 gene transcription.

According to another aspect of the invention, a method for treating a subject having or at risk of developing multidrug resistance is provided. The method involves administering to a subject in need of such treatment, an mdr1-HRE binding molecule (e.g. antisense molecule) in an amount effective to treat the multidrug resistance. The method is particularly useful for treating multidrug resistance for a condition associated with localized hypoxia, e.g., a cancer which presents a solid tumor. The method also is useful for treating malignancies which do not present solid tumors.

According to certain embodiments of this aspect of the invention, the method involves administering an mdr1-HRE binding molecule (e.g. antisense molecule) to a subject having multidrug resistance (e.g., a chemotherapy patient presenting multidrug resistance), or at risk of developing multidrug resistance (e.g., someone for whom chemotherapy is prescribed). Preferably, the subject is a mammal and, more preferably, the subject is a human.

According to still another aspect of the invention, isolated nucleic acids which selectively bind to the mdr1-HRE and complements of the foregoing nucleic acids are provided. The preferred mdr1-HRE antisense molecules have the nucleotide sequences of SEQ ID NOs.: 9–15, inclusive, or unique fragments of SEQ ID NOs.: 9–15, and complements to the foregoing.

According to another aspect of the invention, an isolated HIF-1-SUMO-1 complex is provided. The isolated HIF-1-SUMO-1 complex comprises a HIF-1 molecule selected from the group consisting of HIF-1 or a SUMO-1 binding HIF-1 fragment and a SUMO-1 molecule selected from the group consisting of SUMO-1 or a HIF-1 binding SUMO-1 fragment wherein the SUMO-1 molecule is bound to the HIF-1 molecule. An example of a HIF-1 molecule is HIF-1α. Other examples of a HIF-1 molecule include, but are not limited to, HIF-1α peptide domains comprising amino acids: 390–394, 476–480, 476–482, 528–531, 718–721, or 718–724. Examples of a HIF-1 molecule also encompass nucleic acids comprising a amino acid selected from the group consisting of SEQ ID NOs: 16–21.

In yet another aspect of the invention, a method of screening for agents that modulate the amount of the HIF-1-SUMO-1 complex is provided. The method comprises contacting a HIF-1 molecule with a SUMO-1 molecule under conditions that allow the formation of a HIF-1-SUMO-1 complex, determining the amount of the HIF-1-SUMO-1 complex in the absence of the agent, determining the amount of the HIF-1-SUMO-1 complex in the presence of the agent, and comparing the amount of the HIF-1-SUMO-1 complex in the presence and absence of the agent. In this embodiment, a decrease in the amount of the HIF- 1-SUMO-1 complex in the presence of the agent indicates that the agent a HIF-1-SUMO-1 complex blocking agent, an increase in the amount of the HIF-1-SUMO-1 complex in the presence of the agent indicates that the agent is a HIF-1-SUMO-1 complex enhancing agent.

According to still another aspect of the invention, kits for screening for agents that modulate the amount of a HIF-1SUMO-1 complex are provided. The kits include one or more HIF-1 molecules, one or more SUMO-1 molecules and, instructions for the use of the HIF-1 molecules and SUMO-1 molecules for detecting agents that modulate the amount of a HIF-1-SUMO-1 complex.

In a further aspect of the invention, another method for inhibiting MDR expression is provided. The method involves contacting a nucleic acid encoding an MDR polypeptide with a HIF-1-SUMO1 complex blocking agent in amount effective to inhibit MDR expression.

An example of a HIF-1-SUMO complex blocking agent is a SUMO-1 binding molecule. The SUMO-1 binding molecule inhibits sumo-1 expression at the transcriptional, translational, or post-translational level. Thus, SUMO-1 binding molecules inhibit the ability of the SUMO-1 polypeptide (SEQ ID NO: 8) to bind to a HIF-1 molecule. Exemplary SUMO-1 binding molecules which inhibit transcription of sumo-1 gene (SEQ ID NO: 7) (GenBank Accession NO: U67122) include antisense molecules to sumo-1. Exemplary SUMO-1 binding molecules also include binding peptides such as antibodies or antibody fragments which selectively bind to a SUMO-1 polypeptide and, thereby, inhibit binding of SUMO-1 to HIF-1.

A method for treating a subject having or at risk of developing a multiple drug resistance is also provided. The method comprises administering to a subject in need of such treatment and free of indications otherwise calling for treatment with a SUMO-1 binding molecule, one or more SUMO-1 binding molecules in an amount effective to treat the multiple drug resistance.

The method is particularly useful for treating multidrug resistance for a condition associated with localized hypoxia, e.g., a cancer which presents a solid tumor. The method also is useful for treating malignancies which do not present solid tumors.

According to certain embodiments of this aspect of the invention, the method involves administering one or more SUMO-1 binding molecules (e.g. antisense molecules) to a subject having multidrug resistance (e.g., a chemotherapy patient presenting multidrug resistance), or at risk of developing multidrug resistance (e.g., someone for whom chemotherapy is prescribed). One example of multidrug resistance is a hematologic malignancy that is resistant to chemotherapy. Preferably, the subject is a mammal and, more preferably, the subject is a human.

The subject may be undergoing chemotherapy, radiation therapy, or a combination of chemotherapy and radiation therapy, about to undergo chemotherapy, radiation therapy, or a combination of chemotherapy and radiation therapy, or has recently undergone chemotherapy, radiation therapy, or a combination of chemotherapy and radiation therapy. Optionally, the subject may be presenting symptoms of multidrug resistance.

In some embodiments of the invention, the SUMO-1 binding molecule is administered in conjunction with one or more mdr1-HRE binding molecules or HIF-1 binding molecules.

Exemplary SUMO-1 binding molecules are sumo-1 antisense molecules. Examples of sumo-1 antisense molecules include but are not limited to the nucleic acid molecules comprising nucleic acid sequences of SEQ ID NOs: 22–24, unique fragments, and complements of the foregoing.

Other SUMO-1 binding molecules include antibodies or antibody fragments such as an Fab or F(ab)$_2$ fragment of an antibody to SUMO1. Typically, the fragment includes a CDR3 region that is selective for SUMO-1. The antibody is a monoclonal antibody, a polyclonal antibody, or a chimeric antibody. Thus, exemplary SUMO-1 binding molecules include antibodies or antibody fragments that bind SUMO-1 and inhibit the binding of SUMO-1 to HIF-1α.

According to still another aspect of the invention, isolated SUMO-1 antisense nucleic acids comprising sequences selected from the group consisting of: SEQ. ID NOs: 22–24 inclusive, unique fragments, and complements of the foregoing are provided.

According to a further aspect of the invention, pharmaceutical compositions containing the nucleic acids, proteins, and binding molecules of the invention are provided. The pharmaceutical compositions contain any of the foregoing therapeutic agents in a pharmaceutically acceptable carrier. Thus, in a related aspect the invention provides a method for forming a medicament that involves placing a therapeutically effective amount of the therapeutic agent in a pharmaceutically acceptable carrier to form one or more doses.

These and other aspects of the invention will be more apparent in reference to the following detailed description of the invention.

DETAILED DESCRIPTION OF THE INVENTION

The invention is based, in part, on the discovery that the multidrug resistance protein, MDR (also known as P-glycoprotein) (SEQ ID NO: 2), associated with tumor resistance to chemotherapeutics and encoded by the mdr1 gene (SEQ ID NO: 1) (GenBank Accession NO: M14758), is induced by hypoxia. We have used this information to identify transcriptional elements in the mdr1 gene that are associated with hypoxia inducibility and to develop molecules that selectively inhibit mdr1 gene expression that is mediated by hypoxia.

The results disclosed herein demonstrate that RNA derived from a human intestinal epithelial cell line (T84) revealed an approximate 7-fold increase in mdr1, but not mdr-3, in epithelial cells exposed to hypoxia (pO$_2$20 torr, 18 hrs). These findings were confirmed at the mRNA levels (semi-quantitative RT-PCR, hypoxia time-dependent induction, maximal 12-fold increase at 24 hr hypoxia) and at the protein level (increase of 3–5-fold by both western blot and surface ELISA). P-glycoprotein function was studied by analysis of verapamil-inhibitable efflux of digoxin and fluorescein isothiocyanate in intact T84 cells, and indicated that hypoxia enhances P-glycoprotein efflux function by as much as 7±0.4-fold over normoxia. Subsequent results confirmed hypoxia-elicited mdr1 gene induction and increased P-glycoprotein expression in non-transformed, primary cultures of human microvascular endothelial cells, indicating that such findings are not specific for transformed cell types.

In view of the foregoing results, we examined the mdr1 gene (Ueda, K., et al., J. Biol. Chem. 262:505–508, 1987; Ueda, K., et al., Biochem. Biophys. Res. Commun. 141: 956–962, 1986; Ueda, K., et al., J. Biol. Chem. 262:17432–17436, 1987) and identified at least three binding sites for hypoxia inducible factor-1 (HIF-1), a transcription factor associated with hypoxia inducibility (Semenza, G. L. 1998. Curr. Opin. Genet. Dev. 8:588). In our further experiments showed that inhibition of HIF-1 expression by antisense oligonucleotides resulted in significant inhibition of hypoxia-inducible mdr1 expression and a nearly complete loss of basal mdr1 expression in normoxic epithelia and endothelia.

Taken together, these findings indicate that the mdr1 gene is hypoxia-responsive and suggested to us the identification of hypoxia-elicited P-glycoprotein expression as a pathway for resistance of some cancers to chemotherapeutics. Thus, the invention is based, in part, on the discovery that the multidrug resistance (mdr1) gene product P-glycoprotein is induced by hypoxia. As used herein hypoxia is defined as the decreased delivery of molecular oxygen ($O_2$) to cells, tissues or organs for periods of time to evoke acute or long-term physiologic consequences.

HDR1 expression is regulated by hypoxia-related regulators. Exemplary hypoxia-related regulators of MDR-1 expression include: hypoxia-inducible factor-1 (HIF-1) (Wang, et al., Proc. Natl. Acad. Sci. 92:5510, 1995; Wang, and Semenza, J. Biol. Chem. 270:1230, 1995), hypoxia-inducible factor-2 (HIF-2) (Wiesener et al., Blood 92: 2260–2268, 1998, Genbank Accession NO: U81984) (SEQ ID NO: 60) encoded for by hif-2 (SEQ ID NO: 59), and hypoxia-inducible factor-3 (HIF-3) (Gu, et. al, Gene Expr. 7: 205–213, 1998, Genbank Accession NO: AB054067) (SEQ ID NO: 62) encoded for by hif-3 (SEQ ID NO: 61). HIF-1 is a member of the rapidly growing Per-ARNT-Sim (PAS) family of basic helix-loop-helix (bHLH) transcription factors. Functional HIF-1 exists as a heterodimer of HIF-1α (SEQ ID NO: 4) and HIF-1 β α (SEQ ID NO: 6). The activation of HIF-1 is dependent upon stabilization of an $O_2$-dependent degradation pathway in the HIF-1α (Huang, L. E., et al., Proc. Nat. Acad. Sci. (USA) 95:7987, 1998). Binding of HIF-1 to DNA consensus domains (5'-RCGTG-3') (SEQ ID NO: 25) results in the transcriptional induction of HIF-1 bearing gene promoters (Semenza, Curr Opin Genet Dev; 8:588–94, 1998). HIF-1 is widely expressed and recent studies indicate that consensus HIF-1 binding sequences exist in a number of genes (Semenza, G. L.: Curr. Opin. Genet. Dev. 8:588, 1998). (See also, U.S. Pat. No. 6,020,462, issued to Semenza, which reports HIF-1 blocking agents for treating cancers associated with tumor proliferation mediated by VEGF-induced angiogenesis.) The central region of HIF-1α contains an oxygen-dependent-degradation (ODD) domain located between amino acids 401 and 603. In normoxic conditions (normal oxygen concentrations in the blood) HIF-1α is ubiquinated and rapidly degraded through the proteosomal machinery). In hypoxic conditions (low oxygen concentrations in the blood) the protein is stabilized and accumulates within the nucleus, a process that is initiated instantaneously. A newly discovered small ubiquitin-like-modifier (SUMO-1) (SEQ ID NO: 8) appears to antagonize HIF-1α degradation. Prior to this discovery, it was not known that SUMO-1 antagonized HIF-1α degradation by binding to an oxygen-dependent-degradation (ODD) doman in the HIF-1α molecule.

In view of the foregoing discoveries, the following inventions are provided.

According to one aspect of the invention, a method is provided wherein a HIF-1 binding molecule is used for treating a subject afflicted by or susceptible to a hematologic malignancy. The method involves administering to a subject having or at risk of developing a hematologic malignancy a therapeutically effective amount of a HIF-1 binding molecule. The preferred subjects of the present invention do not have any other indication for a HIF-1 binding molecule. Exemplary such indications calling for treatment with a HIF-1 binding molecule include cancers that are associated with tumor proliferation mediated by VEGF-induced angiogenesis (see, e.g., U.S. Pat. No. 6,020,462, issued to Semenza). Accordingly, in certain preferred embodiments, the subject does not present a solid tumor and/or is otherwise free of a condition such as those disclosed in Semenza '462.

A subject having a hematologic malignancy is a subject with at least one identifiable sign, symptom, or laboratory finding sufficient to make a diagnosis of a hematologic malignancy in accordance with clinical standards known in the art for identifying such disorders. Examples of such clinical standards can be found in *Harrison's Principles of Internal Medicine,* 14th Ed., Fauci AS et al., eds., McGraw-Hill, New York, 1998. In some instances, a diagnosis of a hematologic malignancy will include identification of a particular malignant cell type present in a sample of a body fluid or tissue obtained from the subject.

As used herein, hematologic malignancy is a term of art which refers to a lymphoid disorder or a myeloid disorder.

Lymphoid disorders include acute lymphocytic leukemia and chronic lymphoproliferative disorders (e.g., lymphoma, myeloma, and chronic lymphoid leukemias). Lymphomas include hodgkin's disease and non-hodgkin's lymphoma. Chronic lymphoid leukemias include T cell chronic lymphoid leukemias and B cell chronic lymphoid leukemias.

Myeloid disorders include chronic myeloid disorders and acute myeloid leukemia. Chronic myeloid disorders include chronic myeloproliferative disorders and myelodysplastic syndrome. Chronic myeloproliferative disorders include angiogenic myeloid metaplasia, essential thrombocythemia, chronic myelogenous leukemia, polycythemia vera, and atypical myeloproliferative disorders. Atypical myeloproliferative disorders include atypical CML, chronic neutrophilic leukemia, mast cell disease, and chronic eosinophilic leukemia.

A subject at risk of developing a hematologic malignancy is a subject with an identifiable risk factor for developing a hematologic malignancy. For example, a subject at risk of developing a hematologic malignancy can include an individual with a known or suspected exposure to environmental agents (e.g., carcinogens) associated with an increased risk of developing a hematologic malignancy. Additionally or alternatively, a subject at risk of developing a hematologic malignancy can include an individual with a genetic predisposition to developing a hematologic malignancy. Yet other examples of a subject at risk of developing a hematologic malignancy include a subject that previously has been diagnosed with a cancer associated with a solid tumor and who is at risk of metastasis of the primary tumor.

According to this aspect of the invention, the subject is treated by administering a HIF-1 binding molecule. As used herein, a "HIF-1 binding molecule" refers to a compound which inhibits HIF-1 expression (at the transcriptional, translational, or post-translational level). HIF-1 expression refers to the ability of the HIF 1 polypeptide to bind to a HIF-1 responsive element (HRE) and induce transcription of the nucleic acid which contains the HRE (typically in the promoter region of a gene sequence). Exemplary HIF-1 binding molecules include antisense nucleic acid, ribozymes, or triplex agents to block transcription or translation of a specific hif-1 mRNA or DNA, either by masking that mRNA with an antisense nucleic acid or DNA with a triplex agent, or by cleaving the nucleotide sequence with a ribozyme (See, e.g., U.S. Pat. No. 6,020,462, issued to Semenza.) Exemplary HIF-1 binding molecules which inhibit HIF-1 activity include binding peptides such as antibodies/antibody fragments which selectively bind to a HIF-1 polypeptide and, thereby, inhibit binding of the HIF-1 to the HRE. Exemplary HIF-1 binding molecules also include polypeptides which selectively inhibit the formation of HIF-1. Preferably the HIF binding polypeptides are all permeant. An example of a molecule used to prepare cell permeant peptides is HIF-tat peptide.

The HRE is defined as the central HIF-1 binding region of the mdr1 and flanking nucleotides on either or both 5' and 3' ends of the HIF-1 binding site. The invention embraces 11 previously unappreciated HIF-1 binding sites in the mdr-1 gene, each of which is unique to mdr1. These sequences (SEQ ID NOs: 26–36) are shown below (the central HIF-1 binding region is in upper case and the indicated position is relative to transcription start site):

ctttgaaagACGTGtctacataag with HIF-1 site at positions −256 to −260 (SEQ ID NO: 26)

cagcgccgggGCGTGggctgagcac with HIF-1 site at positions −45 to −49 (SEQ ID NO: 27)

aactctgcctTCGTGgagatgctgg with HIF-1 site at positions +498 to +502 (SEQ ID NO: 28)

taggatttacACGTGgttggaagct with HIF-1 site at positions +766 to +770 (SEQ ID NO: 29)

ttcgctatggCCGTGaaaatgtcac with HIF-1 site at positions +1612 to +1616 (SEQ ID NO: 30)

tcgccattgcACGTGccctggttcg with HIF-1 site at positions +1765 to +1769 (SEQ ID NO: 31)

gtaggagtgtCCGTGgatcacaagc with HIF-1 site at positions +2156 to +2160 (SEQ ID NO: 32)

ttggtgccatggCCGTGgggcaagtc with HIF-1 site at positions +3100 to +3104 (SEQ ID NO: 33)

cacctgggcaTCGTGTcccaggagcc with HIF-1 site at positions +3484 to +3488 (SEQ ID NO: 34)

caggaagagaTCGTGagggcagcaa with HIF-1 site at positions +3573 to +3577 (SEQ ID NO: 35)

cattgccatagcTCGTGcccttgttagac with HIF-1 site at positions +3701 to +3705 (SEQ ID NO: 36)

The invention also encompasses unique fragments of the foregoing sequences, particularly unique fragments of SEQ ID Nos. 26 through 36 which include the HIF-1 binding site and at least 2, 3, 4, 5, 6, 7, 8, 9, 10, 11, 12, 13, 14, 15, 16, 17, 18, 19, or 20 additional nucleotides (contributed from the mdr sequence flanking the HIF-1 binding site) present on either or both 5' and 3' ends of the HIF-1 binding site. Thus, for example, unique fragments of SEQ ID NO: 26 would include, but not be limited to:

ttttgaaagACGTGtctacataag (SEQ ID NO: 51);
ttgaaagACGTGtctacataag; (SEQ ID NO: 52)
tgaaagACGTGtctacataag; (SEQ ID NO: 53)
tgaaagACGTGtctacataag; (SEQ ID NO: 54)
ctttgaaagACGTGtctacataa; (SEQ ID NO: 55)
ctttgaaagACGTGtctacata; (SEQ ID NO: 56)
ctttgaaagACGTGtctacat; (SEQ ID NO: 57)
ctttgaaagACGTGtctaca (SEQ ID NO: 58); and so forth, provided that the unique fragments are unique in sequence, e.g., as determined using BLAST, for the mdr gene.

According to another aspect of the invention, a method for treating a subject having or at risk of developing multidrug resistance is provided. The method involves administering to a subject in need of such treatment, an mdr1-HRE binding molecule in an amount effective to treat the multidrug resistance. The method is particularly useful for treating multidrug resistance as a result of drug treatment for a condition associated with localized hypoxia, e.g., a cancer which presents a solid tumor. The method also is useful for treating hematologic malignancies which do not present solid tumors.

According to certain embodiments of this aspect of the invention, the method involves administering an mdr1-HRE binding molecule to a subject having multidrug resistance (e.g., a chemotherapy patient presenting multidrug resistance), or at risk of developing multidrug resistance (e.g., someone for whom chemotherapy is prescribed). Preferably, the subject is a mammal and, more preferably, the subject is a human.

According to still another aspect of the invention, isolated nucleic acids which selectively bind to the mdr 1-HRE and complements of the foregoing nucleic acids are provided. The preferred mdr1-HRE antisense molecules have the nucleotide sequences of SEQ ID NOs: 9–15, inclusive, or unique fragments of SEQ ID NOs: 9–15, and complements to the foregoing.

Antisense oligomers of about 15 to about 35 nucleotides are preferred, since they are easily synthesized and are less likely to cause problems than larger molecules when introduced into the target HIF-1-producing cell.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher et al., Antisense Res. and Dev. 1:227, 1991; Helene, Anticancer Drug Design, 6,569, 1991).

Ribozymes are RNA molecules possessing the ability to specifically cleave other single stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn. 260:3030, 1988). A major advantage of this approach is that, because they are sequence-specific, only mRNAs with particular sequences are inactivated.

There are two basic types of ribozymes namely, tetrahymena-type (Hasselhoff Nature 334:585, 1988) and "hammerhead"-type. Tetrahymena-type ribozymes recognize sequences which are four bases in length, while "hammerhead"-type ribozymes recognize base sequences 11–8 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The invention embraces HIF-1 binding molecules that are antisense molecules that selectively bind to a nucleic acid molecule encoding a HIF-1 polypeptide (for treating a hematologic malignancy). The invention also embraces antisense molecules that bind to a HRE located in an mdr sequence ("mdr1-HRE antisense molecules"), such as the nucleic acid molecules defined by SEQ ID NOs: 9–15, unique fragments, or complements of these nucleic acid molecules. mdr1-HRE antisense molecules are described in more detail below. A unique fragment is one that is a 'signature' for the larger nucleic acid. It, for example, is long enough to assure that its precise sequence is not found in molecules outside of the defined nucleic acid molecules. Those of ordinary skill in the art may apply no more than routine procedures to determine if a fragment is unique within the human or mouse genome.

It is to be understood that, in general, the definitions of antisense molecules, delivery routes, pharmaceutical compositions for the HIF-1 antisense molecules of the invention are substantially the same for the mdr1-HRE antisense molecules of the invention.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. Based upon the mdr1-HRE antisense molecules (e.g., SEQ ID NOs: 9 through 15), the known sequences for HIF-1α cDNA (SEQ ID NO: 3) (GenBank Accession NO: U22431), and HIF-1β cDNA (SEQ ID NO: 5) (GenBank Accession NO: M69238), or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are -complementary to the target, although in certain cases modified oligonucleotides as short as 7 bases in length have been used successfully as antisense oligonucleotides (Wagner et al., Nat. Med. 1(11):1116–1118, 1995). Most preferably, the antisense oligonucleotides comprise a complementary sequence of 20–35 bases. Although oligonucleotides may be chosen which are antisense to any region of the gene (such as to the mdr1-HRE) or mRNA transcripts, in certain embodiments directed to inhibiting HIF-1 transcription/translation, the antisense oligonucleotides preferably correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. The present invention also provides for antisense oligonucleotides which are complementary to the genomic DNA corresponding to the hif-1 cDNA sequence or sumo-1 cDNA sequence.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

The invention also involves vectors coding for the nucleic acids of the invention and host cells containing those expression vectors. Virtually any cell, prokaryotic or eukaryotic, which can be transformed with heterologous DNA or RNA and which can be grown or maintained in culture, may be used in the practice of the invention. Examples include bacterial cells such as *E. coli* and eukaryotic cells such as mouse, hamster, pig, goat, primate, yeast, *xenopous,* etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Alternatively, suppression of HIF-1 function can be achieved through administration of a HIF-1 binding molecule that is a polypeptide. HIF-1 a variant polypeptide (dominant negative variant form), or a polypeptide sequence encoding HIF-1α variant polypeptide is an exemplary HIF-1α polypeptide antagonist. By administering HIF-1α variant polypeptide or a nucleotide sequence encoding such polypeptide, the variant will compete with wild-type HIF-1 for binding to HIF-1β in forming HIF-1 dimer, thereby lowering the concentration of HIF-1 dimer in the cell which can efficiently bind to the HIF-1 DNA binding motif (HRE).

Exemplary HIF-1 binding polypeptides also include cell permeant polypeptides which selectively inhibit the formation of HIF-1. An example of a molecule used to prepare cell permeant peptides is HIV-tat peptide. Cells are loaded with polypeptide utilizing molecules such as the HIV-tat peptide sequence. HIF-tat peptide-facilitated loading of cells with peptides is based on previous work (Swarze, Science 285: 1569–1573, 1998) and successfully employed by us to target functional inhibition of CREB (Taylor, et. al. Proc Nat Acad Sci (USA) 97: 12091–12096, 2000) and beta 3 integrin (see Bruyninckx, et. al., Blood 97:3251–3258, 2001). Peptide sequences are HIV tat peptide: YGRKKRRQRRRG (SEQ ID NO: 63); synthesized with the HIF-1 nuclear localization sequence AQRKRKMEHDG (SEQ ID NO: 64); or SUMO-1 binding sites within HIF-1 (FDKLKKEPDAL (SEQ ID NO: 65), EVALKLEPNPES (SEQ ID NO: 66), or DMVNEFKLELVE (SEQ ID NO: 67)). All peptides are made as stock concentration of 10 mM in dimethylsulfoxide (DMSO). Equimolar concentrations of HIV tat peptide are co-incubated for 10 min. prior to addition to cells. Peptides (final concentration 10 μM) are added apically using equi-volume DMSO as a vehicle control and peptides are incubated with cells for 15 min. prior to cell incubation in hypoxia (Taylor, et. al. Proc Nat Acad Sci (USA) 97: 12091–12096, 2000).

Suppression of HIF-1 function can also be achieved through administration of an antibody or antibody fragment (e.g., a monoclonal antibody or binding fragment thereof) which selectively binds to HIF-1 and, thereby, inhibits binding of HIF-1 to a HRE. In some embodiments, the antibody or antibody fragment is attached to a HIF-1 binding polypeptide. In yet other embodiments, the antibody or antibody fragment is administered with one or more HIF-1 binding molecules.

The HIF-1 binding molecules of the invention are placed in a pharmaceutically acceptable carrier and are delivered to a recipient subject (preferably a human) in accordance with known methods of drug delivery, depending on the nature of the antagonist (e.g., antisense to the hif-1 or mdr1-HRE antisense molecules, or an antibody for selectively binding to the HIF-1 polypeptide). In general, the methods of the invention for delivering the HIF-1 binding molecules in vivo utilize art-recognized protocols for delivering these types of therapeutic agents (e.g., gene therapy vectors, antibody therapeutics).

Various techniques may be employed for introducing the therapeutic nucleic acids of the invention (e.g., antisense to hif-1, antisense to mdr1-HRE) into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

The following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenza virus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. Nos. 5,276,019 and 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to CMV. U.S. Pat. No. 5,098,890 provides oligonucleotides complementary to at least a portion of the mRNA transcript of the human c-myb. U.S. Pat. No. 5,242,906 provides antisense oligonucleotides useful in the treatment of latent EBV infections.

These and other delivery systems can include time-release, delayed release or sustained release delivery systems. Such systems can avoid repeated administrations of the HIF-1 binding molecules and/or mdr1-HRE antisense molecules, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, as used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

The methods for delivering a functional antisense molecule for transcription in vivo include the methods used to deliver a functional gene for gene therapy applications. For example, a procedure for performing ex vivo gene therapy is outlined in U.S. Pat. No. 5,399,346 and in exhibits submitted in the file history of that patent, all of which are publicly available documents. In general, the method involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application W095/00654. In vivo gene therapy using vectors such as adenovirus, retroviruses, herpes virus, and targeted liposomes also is contemplated according to the invention. See, e.g., U.S. Pat. No. 5,670,488, entitled "Adenovirus Vector for Gene Therapy", issued to Gregory et al., and U.S. Pat. No. 5,672,344, entitled "Viral-Mediated Gene Transfer System", issued to Kelley et al.

HIF-1 binding molecules which are antisense molecules or antibodies selective for HIF-1 reportedly are useful for inhibiting tumor proliferation mediated by VEGF-induced angiogenesis (U.S. Pat. No. 6,020,462, issued to Semenza). Antibodies (e.g., antibodies which bind to HIF-1 and block binding of HIF-1 to an mdr1-HRE) can be administered to a subject in accordance with known methods in the art. Methods for delivering antisense molecules to inhibit transcription of mdr are described in U.S. Pat. No. 6,001,991, issued to Dean, et al. Such methods also are useful for delivering the HIF-1 binding molecules which are formed of nucleotides (e.g., antisense, ribozyme).

The HIF-1 binding molecules may be administered alone or in combination with at least one other agent known or believed by the applicants to be useful for treating a hematologic malignancy. Other agents which are known to be useful in the treatment of proliferative disorders, such as hematologic malignancies, include ribavirin, amantadine, chemotherapeutic agents (e.g., 5-fluorouracil and BCNU), radiation therapy, phototherapy, and cytokines, including IL-2, IL-12, and IFN-γ. Those skilled in the art will recognize which of the other agents to be administered in conjunction with the HIF-1 binding molecules and/or mdr1-HRE antisense molecules are appropriate for treating a given suspected or identified hematologic malignancy.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions.

In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnology* 14: 840–844, 1996).

Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. The present invention also provides for antisense oligonucleotides which are complementary to genomic DNA and/or cDNA corresponding to SEQ ID Nos: 3 and 7. Antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus, modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acid molecules encoding HIF-1 or SUMO-1 proteins, together with pharmaceutically acceptable carriers.

An effective amount means, with respect to a hematologic malignancy for example, that amount of a HIF-1 binding molecule which prevents the onset of, alleviates the symptoms of, or stops the progression of the malignancy. In general such symptoms are, at least in part, the result of unwanted cell proliferation cells in vivo. Thus, a "hematologic malignancy" is a condition that is characterized by certain clinical features and which, it is generally believed, is associated with unwanted cell proliferation cells in vivo. "Unwanted," with respect to cell proliferation cells in vivo, refers to cell proliferation which results in an adverse medical condition. The phrase "therapeutically effective amount" means, with respect to multiple drug resistance, that amount of an mdr1-HRE binding molecule which prevents the onset of, alleviates the symptoms of, or stops the progression of the multiple drug resistance. Multiple drug resistance is a condition that is characterized by certain clinical features (e.g., reduced drug efficacy).

The term "treating" is defined as administering, to a subject, a therapeutically effective amount of a compound (e.g., a HIF-1 binding molecule, an mdr1-HRE binding molecule, or a SUMO-1 binding molecule) that is sufficient to prevent the onset of, alleviate the symptoms of, or stop the progression of a disorder or disease being treated. The term "subject", as described herein, is defined as a mammal. In a preferred embodiment, a subject is a human.

The pharmaceutical preparations disclosed herein are prepared in accordance with standard procedures and are administered at dosages that are selected to reduce, prevent or eliminate the condition (See, e.g., Remington's Pharmaceutical Sciences, Mack Publishing Company, Easton, Pa., and Goodman and Gilman's The Pharmaceutical Basis of Therapeutics, Pergamon Press, New York, N.Y., the contents of which are incorporated herein by reference, for a general description of the methods for administering various agents for human therapy).

The pharmaceutically acceptable compositions of the present invention comprise one or more HIF-1 binding molecules (and/or mdr1-HRE binding molecules, and/or or a SUMO-1 binding molecules) in association with one or more nontoxic, pharmaceutically acceptable carriers and/or diluents and/or adjuvants and/or excipients, collectively referred to herein as "carrier" materials, and if desired other active ingredients.

The HIF-1 binding molecules (and/or mdr1-HRE binding molecules, and/or or a SUMO-1 binding molecules) of the present invention may be administered by any route, preferably in the form of a pharmaceutical composition adapted to such a route, and would be dependent on the condition being treated. The compounds and compositions may, for example, be administered orally, intravascularly, intramuscularly, subcutaneously, intraperitoneally, or topically. Preferred routes of administration include oral and intravenous administration.

For oral administration, the HIF-1 binding molecules (and/or mdr1-HRE binding molecules, and/or or a SUMO-1 binding molecules) may be in the form of, for example, a tablet, capsule, suspension or liquid. The pharmaceutical composition is preferably made in the form of a dosage unit containing a therapeutically effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth;

fillers, for example, calcium phosphate, cellulose, glycine, lactose, maize-starch, mannitol, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions may also be administered via injection. Formulations for parenteral administration may be in the form of aqueous or non-aqueous isotonic sterile injection solutions or suspensions. These solutions or suspensions may be prepared from sterile powders or granules having one or more of the carriers mentioned for use in the formulations for oral administration. The compounds may be dissolved in polyethylene glycol, propylene glycol, ethanol, corn oil, benzyl alcohol, sodium chloride, sterile water, and/or various buffers.

For topical use the compounds of the present invention may also be prepared in suitable forms to be applied to the skin, or mucus membranes of the nose and throat, and may take the form of creams, ointments, liquid sprays or inhalants, lozenges, or throat paints. Such topical formulations further can include chemical compounds such as dimethylsulfoxide (DMSO) to facilitate surface penetration of the active ingredient. Suitable carriers for topical administration include oil-in-water or water-in-oil emulsions using mineral oils, petrolatum and the like, as well as gels such as hydrogel. Alternative topical formulations include shampoo preparations, oral pastes and mouthwash.

For rectal administration the compounds of the present invention may be administered in the form of suppositories admixed with conventional carriers such as cocoa butter, wax or other glyceride.

Alternatively, the compounds of the present invention may be in powder form for reconstitution at the time of delivery.

The dosage regimen for treating a hematologic malignancy with the HIF-1 binding molecules (and/or mdr1-HRE binding molecules and/or or a SUMO-1 binding molecules) is selected in accordance with a variety of factors, including the type, age, weight, sex and medical condition of the subject, the severity of the disease, the route and frequency of administration, the renal and hepatic function of the subject, and the particular compound employed. An ordinarily skilled physician or clinician can readily determine and prescribe the effective amount of the drug required to treat a hematologic malignancy (and/or multiple drug resistance). In general, dosages are determined in accordance with standard practice for optimizing the correct dosage for treating a hematologic malignancy (and/or multiple drug resistance).

The dosage regimen can be determined, for example, by following the response to the treatment in terms of vital signs. Examples of such vital signs are well known in the art, and they include the pulse, blood pressure, temperature, and respiratory rate. *Harrison's Principles of Internal Medicine,* 14th Ed., Fauci AS et al., eds., McGraw-Hill, New York, 1998.

Typically dosages of the HIF-1 binding molecule (and/or mdr1-HRE binding molecules and/or or a SUMO-1 binding molecules) will be dependent upon the nature of the binding molecules. (See, e.g., U.S. Pat. No. 6,020,462, issued to Semenza; and U.S. Pat. No. 6,011,991, issued to Dean, et al.). In general, the active agent concentration will range from between 0.01 mg per kg of body weight per day (mg/kg/day) to about 10.0 mg/kg/day. Alternatively, the dosages of the HIF-1 binding molecule will range from between 0.01 micromole per kg of body weight per day (μmole/kg/day) to about 10 μmole/kg/day. Preferred oral dosages in humans may range from daily total dosages of about 1–1000 mg/day over the effective treatment period. Preferred intravenous dosages in humans may range from daily total dosages of about 1–100 mg/day over the effective treatment period.

According to another aspect of the invention, an isolated HIF-1-SUMO-1 complex is provided. The isolated HIF-1-SUMO-1 complex comprises a HIF-1 molecule selected from the group consisting of HIF-1 or a SUMO-1 binding HIF-1 fragment and a SUMO-1 molecule selected from the group consisting of SUMO-1 or a HIF-1 binding SUMO-1 fragment wherein the SUMO-1 molecule is bound to the HIF-1 molecule. An example of a HIF-1 molecule is HIF-1α. Other examples of a HIF-1 molecule include, but are not limited to, HIF-1α peptide domains comprising amino acids: 90–94, 476–480, 476–482, 528–531, 718–721, or 718–724. Examples of a HIF-1 molecule also encompass nucleic acids comprising a amino acid selected from the group consisting of SEQ ID NOs: 16–21. As used herein with respect to polypeptides, proteins, or protein complexes, "isolated" means separated from its native environment and present in sufficient quantity to permit its identification or use.

In yet another aspect of the invention, a method of screening for agents that modulate the amount of a HIF-1-SUMO-1 complex is provided. The method comprises contacting a HIF-1 molecule with a SUMO-1 molecule under conditions that allow the formation of a HIF-1-SUMO-1 complex, determining the amount of the HIF-1-SUMO-1 complex in the absence of the agent, determining the amount of the HIF-1-SUMO-1 complex in the presence of the agent, an d comparing the amount of the HIF-1-SUMO-1 complex in the presence and absence of the agent. In this embodiment, a decrease in the amount the HIF-1-SUMO-1 complex in the presence of the agent indicates that the agent is a HIF-1-SUMO-1 complex blocking agent, an increase in the amount the HIF-1-SUMO-1 complex in the presence of the agent indicates that the agent is a HIF-1-SUMO-1 enhancing complex.

According to still another aspect of the invention, kits for screening for agents that modulate the amount of a HIF-1-SUMO-1 complex are provided. The kits include one or more HIF-1 molecules, one or more SUMO-1 molecules and, instructions for the use of the HIF-1 molecules and SUMO-1 molecules for detecting agents that modulate the amount of a HIF-1-SUMO-1 complex.

A wide variety of assays for screening pharmacological agents can be used in accordance with this aspect of the invention, including, labeled in vitro protein-protein binding assays, electrophoretic mobility shift assays, immunoassays, cell-based assays such as two- or three-hybrid screens, expression assays, etc. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid molecule, the agent typically is a DNA or RNA molecule, although modified nucleic acid molecules as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

An exemplary binding assay is described herein. In general the mixture of the foregoing assay materials is incubated under conditions whereby, but for the presence of the candidate pharmacological agent, a HIF-1 molecule binds a SUMO-1 molecule and forms a HIF-1-SUMO-1 complex. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the effect of the candidate agent on the formation of HIF-1-SUMO-1 complex is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two-or three-hybrid screens. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseseradish peroxidase, etc.). The label may be bound to a HIF-1 molecule or a SUMO-1 molecule, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The above described methods to HIF-1 are also applicable to HIF-2 and HIF-3 by substituting the molecules and reagents that bind to HIF-1 with molecules and reagents that bind to HIF-2 or HIF-3.

The invention will be more fully understood by reference to the following examples. These examples, however, are merely intended to illustrate the embodiments of the invention and are not to be construed to limit the scope of the invention.

EXAMPLES

Introduction

A major obstacle in development of effective cancer chemotherapies is tumor development of the multidrug resistance(MDR) phenotype (Kuwano et al., Anticancer Drug Des., 14, 123–131, 1999). The MDR phenotype is generally considered to be acquired following administration of chemotherapeutic agents, and is most prevalent in acute myleogenous leukemia (AML) and in aggressive carcinomas (e.g. breast and ovarian). The MDR phenotype is associated with the induction of the mdr1 gene, which encodes for, and results in overexpression of P-glycoprotein (Pgp). Pgp is a 170–180 kD member of the ABC-type transporter family and functions as an energy-dependent membrane efflux pump which transports a wide variety of structurally unrelated xenobiotics to maintain cytoplasmic concentrations at subtoxic levels (Fardel et al., Gen. Pharmacol., 27, 1283–1291, 1996). mdr1 is expressed in some normal cell types (e.g. intestinal epithelia and lymphocytes), but overexpression of Pgp has been shown to correlate with multidrug resistance and increased Pgp expression has been demonstrated in numerous multidrug resistant cell lines (Goldstein, Eur. J. Cancer, 6, 1039–1050, 1996). It is not fully understood how Pgp overexpression is mediated in cancer, however, a number of studies have suggested that transcriptional mechanism(s) of mdr1 induction in human tumors is complex (Fardel et al., Gen. Pharmacol., 27, 1283–1291, 1996; Goldstein, Eur. J. Cancer, 6, 1039–1050, 1996). For example, the cloned mdr1 promoter bears binding sites for a number of transcription factors, including SP1, NF-Y, and YB-1 (Jin et al., Mol. Cell Biol., 18, 4377–4384, 1998). Similarly, it was recently demonstrated that negative regulation of mdr1 is mediated by the p65 subunit of NF-kB in complex with c-fos (Ogretmen et al., Biochemistry, 38, 2189–2199, 1999).

Many types of human tumors are significantly oxygen deprived (Semenza, Crit. Rev. Biochem. Mol. Biol., 35, 71–103, 2000). Due to the combination of tissue mass and the particularly high rate of glycolysis in tumor cells (termed the Warburg effect), hypoxia is considered a property of many tumor types. While most tissues of the body maintain an oxygen gradient spanning a distance of approximately 300–400 μm, studies assessing relative oxygen tensions within tumors have suggested that oxygen concentrations may be as much as 10–100-fold decreased at comparable distances from capillary blood supplies (Semenza, Crit. Rev. Biochem. Mol. Biol., 35, 71–103, 2000). Such an environment establishes a setting of concentric areas of chronic hypoxia within tumors, and sets into motion the transcriptional induction of numerous hypoxia-responsive genes, including glycolytic enzymes, pro-angiogenic factors and pro-inflammatory genes (Semenza, Curr. Opin. Genet Dev., 8, 588–594, 1998) Examples of hypoxia-responsive genes have been associated with growing tumors, include vascular endothelial growth factor (VEGF) and the tumor suppressor p53. Among other transcriptional pathways, hypoxia is known to induce hypoxia inducible factor-1 (HIF-1), a member of the rapidly growing Per-ARNT-Sim (PAS) family of basic helix-loop-helix (bHLH) transcription factors (Semenza, J. Clin. Invest., 106, 809–812, 2000).

HIF-1 exists as an αβ heterodimer, the activation of which is dependent upon stabilization of an $O_2$-dependent degradation domain of the α subunit by the ubiquitin-proteasome pathway (Huang et al., Proc. Nat. Acad. Sci. (USA), 95, 7987–7992, 1998). While not clear, HIF-1 appears to reside in the cytoplasm of normoxic cells, and like a number of other transcription factors (e.g. NF-κB, β-catenin), HIF-1 translocates to the nucleus to form a functional complex (Presta et al., Cancer Res., 57, 4593–4599, 1997; Kallio et al., J. Biol. Chem. 274, 6519–6525, 1999). Binding of HIF-1 to consensus domain of a number of genes results in the transcriptional induction of HIF-1-bearing gene promoters (Semenza, Curr. Opin. Genet Dev., 8, 588–594, 1998). HIF-1 is widely expressed and consensus HIF-1 binding sequences exist in a number of genes, and are termed hypoxia responsive enhancers (HRE) (Semenza, Curr. Opin. Genet Dev., 8, 588–594, 1998).

We demonstrated that the mdr1 gene product P-glycoprotein, a 170 kD transmembrane protein associated with tumor resistance to chemotherapeutics, was induced by hypoxia. Our studies using an epithelial cell line revealed an approximately 7-fold increase in mdr1, but not mdr3, in epithelial cells exposed to hypoxia. These findings were confirmed at the mRNA level and at the protein level. P-glycoprotein function was studied by analysis of verapamil-inhibitable efflux of digoxin and fluorescein isothiocyanate in intact T84 cells, and indicated that hypoxia enhances P-glycoprotein efflux function by as much as 7±0.4-fold over normoxia.

Further studies confirmed hypoxia-elicited mdr1 gene induction and increased P-glycoprotein expression in non-transformed, primary cultures of human microvascular endothelia cells, indicating that such findings are not specific for transformed cell types. These data together with an examination of the mdr1 gene identified previous unappreciated transcriptional elements associated with hypoxia inducibility and a functional HRE in the mdr1 gene.

Taken together, these data indicated that the mdr1 gene is hypoxia-responsive and the results identified hypoxia-elicited P-glycoprotein expression as a pathway for resistance of some tumors to chemotherapeutics.

Materials and Methods

Growth and maintenance of cell lines: T84 cells and CaCO2 B Be cells were grown as monolayers on polycarbonate permeable supports as previously described (Colgan et al., J. Exp. Med., 184, 1003–1015, 1996; Turner et al., J. Biol. Chem., 271, 7738–7744, 1996). Human microvascular endothelial cells (HMVEC), an endothelial primary culture isolated from adult dermis, were used throughout these studies. Where used, HMVEC were obtained from Cascade Biologics (Portland, Oreg.) and cultured as previously described (Lennon et al., J. Exp. Med., 188, 1433–1443, 1998).

Monolayer exposure to hypoxia: Cultured cell exposure to hypoxia was performed as previously described (Colgan et al., J. Exp. Med., 184, 1003–1015, 1996). Upon entry into the humidified hypoxic cell chamber (Coy Laboratory Products, Ann Arbor, Mich.), cell media was exchanged with pre-equilibrated hypoxic media. Standard hypoxic conditions (based on previous work (Colgan et al., J. Exp. Med., 184, 1003–1015, 1996; Taylor et al., Proc. Natl. Acad. Sci. USA, 97, 12091–12096, 2000)), were $pO_2$ 20 torr, $pCO_2$ 35 torr, with the balance made up of nitrogen and water vapor. Normoxic controls were cells exposed to the same experimental protocols under conditions of atmospheric oxygen concentrations ($pO_2$ 147 torr and $pCO_2$ 35 torr within a tissue culture incubator)

Analysis of messenger RNA levels by RT-PCR: The transcriptional profile of epithelial cells exposed to ambient hypoxia was assessed in RNA derived from control or hypoxic epithelia (T84 cells at 6 or 18 hr hypoxia) using quantitative genechip expression arrays (Affymetrix, Inc., Santa Clara, Calif.) (Lockhart et al., Nat. Biotechnol., 14, 1675–1680, 1996). RT-PCR analysis of mRNA levels was performed using DNAse treated total RNA as previously described (Taylor et al., J. Biol. Chem., 274, 19447–19450, 1999) using primers specific for mdr1 (forward primer 5'-AAC GGA AGC CAG AAC ATT CC-3' (SEQ ID NO: 37) and reverse primer 5'-AGG CTT CCT GTG GCA AAG AG-3' (SEQ ID NO: 38), 180 bp fragment), HIF-1α (forward primer 5'- CTC AAA GTC GGA CAG CCT CA-3' (SEQ ID NO: 39) and reverse primer 5'-CCC TGC AGT AGG TTT CTG CT -3' (SEQ ID NO: 40), 460 bp fragment) or control β-actin (forward primer 5'-ATG ACT TCC AAG CTG GCC GTG GCT-3' (SEQ ID NO: 41) and antisense primer 5'-TCT CAG CCC TCT TCA AAA ACT TCT C-3'

(SEQ ID NO: 42), 661 bp fragment). Each primer set was amplified using 25 cycles, unless otherwise noted, of 94° C. for 1 min, 60° C. for 2 min, 72° C. for 4 min, and a final extension of 720° C. for 7 min. The PCR reactions were then visualized on a 1.5% agarose gel containing 5 µg/ml of ethidium bromide.

The PCR for human SUMO-1 contained 50 pM each of the sense primer (5'-CGTCATCATGTCTGACCAGGA-3') (SEQ ID NO: 43) and the antisense primer (3'-CACT-GAAAGTCACAGTCCAGG-5') (SEQ ID NO: 44), 1 µl of cDNA from the reverse transcriptase reaction, 76 µl of DEPC $H_2O$, 10 µl of 10× reaction mix buffer [100 mM KC1/100 mM $(NH_4)_2SO_4$/100 mM Tris pH 8.8/20 mM $MgSO_4$], 2 µl of dNTP (0.2 mM each) and 1 µl of 50× advantage polymerase mix. The amplification reaction included a 3-min denaturation at 60° C. for 30 sec, and 72° C. for 1 min with a final extension at 72° C. for 10 min. Human β-actin was used as a control for each amplification, with sense (5'-TGACGGGGTCACCCACACTGTGC-CCATCTA-3') (SEQ ID NO: 45) and the anti-sense primer (3'-CTAGAAGCATTTGCGGTGGACGATGGAGGG-5') (SEQ ID NO: 46)in identical reactions (661 -bp amplified fragment).

Western blotting: Following experimental treatment, proteins were isolated from confluent monolayers from 100 mm petri dishes as described before (Taylor et al., J. Biol. Chem., 274, 19447–19450, 1999) Proteins were measured (DC protein assay, BioRad, Hecules, Calif.). Samples (25 µg/lane, as indicated) were resolved by reducing SDS PAGE, transferred to nitrocellulose, and blocked overnight in blocking buffer (250 mM NaCl, 0.02% Tween-20, 5% goat serum and 3% bovine serum albumin). For western blotting, anti-P-glycoprotein (rabbit pAb, Biogenesis, Poole, UK) was added for 3h, blots were washed and species-matched peroxidase-conjugated secondary Ab is added, as described previously before (Taylor et al., J. Biol. Chem., 274, 19447–19450, 1999). Labeled bands from washed blots were detected by ECL (Amersham, Piscataway, N.J.).

For examination of CREB/I-κB ubiquitination and SUMOylation, whole cell lysates were prepared as described previously. CREB or I-κB were immunoprecipitated from these lysates using antibodies from (New England Biolabs, Beverly, Mass.) and (Upstate Biotechnology, Victoria, BC, Canada), respectively. Immunoprecipitates were separated by 10% SDS PAGE and transferred to nitrocellulose. Blots were then probed with anti-ubiquitin (Stressgen, Waltham, Mass.) or anti-SUMO-1 (Zymed, South San Francisco, Calif.). Following washing, a species-matched, peroxidase-conjugated secondary antibody was added (Cappell, West Chester, Pa.). Labeled bands were detected by enhanced chemiluminescence (Amersham, Pharmacia, Piscataway, N.J.).

P-glycoprotein surface expression: Surface expression of Pgp was analyzed by ELISA on intact endothelia and epithelia, utilizing previously described methodologies (Zünd et al., Proc. Natl. Acad. Sci. (USA), 93, 7075–7080, 1996). Briefly, cells subjected to indicated periods of hypoxia or normoxia were washed with HBSS (Sigma, St. Louis, Mo.), blocked with media for 30 min at 40° C. Anti-Pgp mAb (clone 3201 used as purified mAb at 20µg/ml), (QED Biosciences, San Diego, Calif.) was added to cells and allowed to incubate for 2h at 4° C. Where indicated, mAb to MHC class I (Barnstable et al., Cell, 14, 9–20, 1978) (clone W6/32 obtained from the American Type Culture Collection, used as 1:100 diluted ascitic fluid) was used as a control. After washing with HBSS, a peroxidase conjugated sheep anti-mouse secondary antibody (Cappel, West Chester, Pa.) was added. Secondary antibody (1:1000 final dilution) was diluted in media containing 10% fetal bovine serum. After washing, plates were developed by addition of peroxidase substrate [2,2'-azino-bis(3-ethylbenzthiazoline-6-sulfonic acid], 1 mM final concentration], (Sigma, St. Louis, Mo.) and read on a microtiter plate spectrophotometer at 405 nm (Molecular Devices, Framingham, Ma.). Controls consisted of media only and secondary antibody only.

P-glycoprotein functional analysis: Pgp function was assessed as verapamil-inhibitable efflux of digoxin and fluoroscein isothiocyanate (FITC). Briefly, epithelial monolayers were exposed to experimental conditions, washed with Hanks Balanced Salt Solution (HBSS, Sigma, St. Louis, Mo.) and incubated with digoxin (6 µM final concentration) or FITC (3 µM final concentration, Molecular Probes, Eugene, Oreg.) in the absence or presence of verapamil (concentration range 1 to 100 µM, Sigma, St. Louis, Mo.). Cells were incubated for 60 min at 37° C. Cells were washed with HBSS and cooled to 4° C.

For digoxin determinations, cells were lysed in ice cold $H_2O$, and lysates were cleared by Eppendorf centrifugation at 14,000×g for 10 min. Digoxin levels in supernatants were assessed by HPLC analysis (Qazaz et al., J. Biol. Chem., 271, 8731–8737, 1996) using a Hewlett-Packard HPLC (Model 1050) with a HP 1100 diode array detector and a reverse phase HPLC column (Luna 5(C18(2) 150×4.60 mm, Phenomenex, Torrance Calif.). Digoxin was measured with a 20–80% $CH_3CN/H_2O$ elution gradient over 30 min at 1 ml/min. Absorbance was measured at 220 nm. UV absorption spectra were obtained at chromatographic peaks. Digoxin was identified by chromatographic behavior (e.g., retention time, UV absorption spectra, co-elution with internal standards) (Qazaz et al., J. Biol. Chem., 271, 8731–8737, 1996).

For determination of intracellular FITC concentrations, fluorescence of washed monolayers (excitation, 485 nm; emission, 530 nm) was assessed on a fluorescent plate reader (Cytofluor™ 2300, Millipore Inc., Bedford, Mass.). Monolayers not exposed to FITC were used to determine background fluorescence.

HIF-1α antisense oligonucleotide treatment of epithelia: HIF-1α depletion in epithelial cells was accomplished by using antisense oligonucleotide loading as described previously (Caniggia et al., J. Clin. Invest., 105, 577–587, 2000) using phosphorothioate derivatives of antisense (GCC GGC GCC CTC CAT) (SEQ ID NO: 47) or control sense (ATG GAG GGC GCC GGC) (SEQ ID NO: 48) oligonucleotides. Antisense oligonucleotide treatment of subconfluent epithelial cells was done as described previously (Colgan et al., J. Exp. Med., 184, 1003–1015, 1996), with modifications. T84 epithelial cells were washed in serum free media then in media containing 20 µg/ml Geneporter transfection reagent (Gene Therapy Systems, San Diego, Calif.) with 2 µg/ml HIF-1α antisense or sense oligonucleotide. Cells are incubated for 4 h at 37° C. then replaced with serum containing growth media. Treated cells were exposed to hypoxia or normoxia for indicated periods of time. As indictated, mdr1 or HIF-1α mRNA were quantified by RT-PCR as described above (see Transcriptional Analysis).

mdr1 reporter assays: CaCO2 cells were used here to assess mdr1 inducibility by hypoxia. Plasmids expressing sequence corresponding to wild-type mdr1 (−189 to +133), truncations at the 3' end (−189 to +4), truncations at the 5' end (−2 to +133) or internal truncations (−119 to +4) of promoter (Drs. Martin Haas and Bryan Strauss, University of California, San Diego described previously in Strauss and Haas, Biochem Biophys Res Comm 217, 333–340, 1995; Jin and Scotto, Mol Cell Biol 18, 4377–4384, 1998) using standard methods of overnight transfection utilizing Effectene transfection reagent (Qiagen, Valencia, Calif.). After transfection, cells were subjected to hypoxia or normoxia for 24 hrs. Luciferase activity was assessed (Topcount-NXT, Hewlett-Packard) utilizing a luciferase assay kit (Stratagene, La Jolla, Calif.). All luciferase activity was normalized to total cellular protein.

mdr-1 HRE binding site mutations: HIF-1 binding site mutations were introduced in 3' end (−189 to +4) truncations of the wild-type promoter using the GeneEditor in vitro site directed mutagenesis system (Promega, Madison, Wis.). Briefly, mutations encoding a three nucleotide mutation in the mdr1 HIF-1 binding site [consensus motif 5'-GC<u>GTG</u>-3' mutated to 5'-GC<u>CAT</u>-3' within HIF-1 site located at positions −49 to −45 relative to the transcription start site] (Ueda et al, J. Biol. Chem., 262, 17432–17436, 1987; Chen et al., J. Biol. Chem., 265, 506–514, 1990) by PCR introduced a unique NCO1 cleavage site and allowed us to screen mutations based on enzymatic cleavage of plasmid DNA. Oligonucleotides used for the three nucleotide mutation were (mutated sequence in lower case) 5'-AGG ACC AGC GCC GGG GCc at G GCT GAG CAC AGC CGC TTC-3' (SEQ ID NO: 49). A deletional mutation of the HIF-1 site was also generated using the oligonucleotide 5'-AGG AAC AGC GCC GGG GG CTG AGC ACA GCC-3' (SEQ ID NO: 50). All mutations were confirmed by sequencing using pGL2-basic primers. CaCO2 or BAE cells, were used to assess mdr1 inducibility by hypoxia. Plasmids expressing sequence corresponding to wild-type mdr1 (−189 to +133), truncations at the 3' end (−189 to +4), truncations at the 5' end (−2 to +133) or internal truncations (−119 to +4) of the mdr1 promoter were co-transfected with β-galactosidase plasmids (p-Hook-2, Invitrogen, Carlsbad, Calif.) using standard methods of overnight transfection utilizing Effectene transfection reagent (Qiagen, Valencia, Calif.). After transfection, cells were subjected to hypoxia or normoxia for 24 hrs. Luciferase activity was assessed (Topcount-NXT, Hewlett-Packard, Paramus, N.J.) utilizing a luciferase assay kit (Stratagene, La Jolla, Calif.). All luciferase activity was normalized with respect to a constitutively expressed β-galactosidase reporter gene. Multicellular spheroid model: A multicellular spheroid model was developed using KB cells grown at high density of membrane permeable supports. Briefly, KB cells in suspension were plated at high density (~$10^7$ cells/cm$^2$) on 0.33 cm$^2$ collagen-coated permeable supports (Corning-Costar, Cambridge, Ma.) and allowed to grow as domes on these substrates for two weeks. Media was replaced every other day and at two weeks, multicellular spheroids were subjected to a 24 or 48 hr period of hypoxia or normoxia, in the presence or absence of the P-glycoprotein substrate doxorubicin (1 µM final concentration) (Sigma, St Louis, Mo.). At the termination of the experiment, the number of viable, intact cells was determined by measurement of the amount of esterase cleavable fluorescent marker 2'7'-bis(carboxyethyl)-5(6)-carboxyfluorescein pentaacetoxymethyl ester (BCECF-AM, 5 µM final concentration Calbiochem, San Diego, Calif.) retained over a 30 min period, a sensitive measurement cytoxicity) (Wierda et al., J. Immunol. Methods, 122, 15–24, 1989). Multicellular spheroids were washed three times in HBSS and fluorescence intensity was measured on a fluorescent plate reader. In subsets of experiments to examine the structure of multicellular spheroids, cultures were stained with rhodamine phalloidin and confocal laser microscopy was utilized to image multicellular spheroids in the x-y and x-z planes, as described previously (Parkos et al., J. Cell. Biol., 132, 437–450, 1996).

EXAMPLE 1

Identification of mdr1 Hypoxia Inducibility

A broad screen of genes relevant to the epithelium identified a hypoxia time-dependent induction of the mdr1 gene (2.2- and 7.1-fold increase over control normoxia at 6 and 18 hrs hypoxia, respectively). Similar exposure to the proinflammatory cytokine IFN-γ, which we have shown to regulate a number of genes in a fashion similar to hypoxia (Taylor et al., Gastroenterol., 114, 657–668, 1998; Taylor et al., J. Biol. Chem., 274, 19447–19450, 1999), did not induce mdr1, and provided some degree of hypoxia selectivity.

RT-PCR analysis was employed to verify these microarray results at the RNA level using primers specific for mdr1 (forward primer 5'-AAC GGA AGC CAG AAC ATT CC-3' (SEQ ID NO: 37)and reverse primer 5'-AGG CTT CCT GTG GCA AAG AG-3' (SEQ ID NO: 38), 180 bp fragment), HIF-1α. (forward primer 5'- CTC AAA GTC GGA CAG CCT CA-3' (SEQ ID NO: 39) and reverse primer 5'- CCC TGC AGT AGG TTT CTG CT -3' (SEQ ID NO: 40), 460 bp fragment) or control β-actin (forward primer 5'-ATG ACT TCC AAG CTG GCC GTG GCT-3' (SEQ ID NO: 41) and antisense primer 5'-TCT CAG CCC TCT TCA AAA ACT TCT C-3' (SEQ ID NO: 42), 661 bp fragment), and revealed a time-dependent induction of mdr1 mRNA expression by hypoxia. Similar results were obtained using epithelial cells other than T84 (CaCO2 cells), and important for this work, hypoxia also induced mdr1 mRNA expression in a non-transformed, primary cell type (HMVEC), suggesting that hypoxia-induced mdr1 is not restricted to cancer cell lines.

Western blot analysis of lysates derived from endothelial and epithelial cell subjected to hypoxia (12–48 hrs) revealed a time-dependent increase in expression of a 170kD protein consistent with the mdr1 gene product P-glycoprotein (Pgp), with maximal protein levels observed by 48 hrs (no additional increases at 72 or 96 hrs). Similarly, staining of endothelial cells subjected to hypoxia revealed a time-dependent increase in Pgp expression.

To examine whether cell surface expression of Pgp was evident, a whole cell ELISA technique was adopted using mAb clone 3201 used as purified mAb at 20 µg/ml), (QED Biosciences, San Diego, Calif.) which recognizes an external epitope on Pgp. Increasing periods of time in hypoxia resulted in increased detectable Pgp ($p<0.01$ by ANOVA), but no obvious changes in MHC class I expression (p=not significant).

We next assessed whether hypoxia-induced Pgp was functional. Pgp has been shown to non-selectively transport a wide variety of amphipathic molecules and is competitively inhibited by verapamil. Thus, Pgp function was assessed as verapamil-inhibitable efflux of the substrates digoxin and fluoroscein isothiocyanate (FITC). Functional activity of Pgp was assayed by assessing accumulation of substrate in Pgp expressing cells, and its inhibition by verapamil (Goldstein, Eur. J. Cancer, 6, 1039–1050, 1996). Endothelial cells exposed to hypoxia demonstrated an enhanced digoxin and FITC efflux. In both cases, the addition of increasing concentrations of verapamil (range 10–100 µM) resulted in increased intracellular accumulation of digoxin or FITC, but to a lesser extent in cells pre-exposed to 48 hr hypoxia, indicating that increased expression of Pgp is reflected at the functional level.

Taken together, these data indicated that hypoxia provides a stimulus for the induction of the mdr1 gene as well as an increase in surface expressed Pgp and functional protein.

EXAMPLE 2

Identification of HRE'S within the MDR Promoter

In an attempt to gain specific insight into the mechanisms of mdr1 induction, we began examining induction pathways from hypoxia response genes. Among other transcriptional pathways, hypoxia is known to induce hypoxia inducible factor-1 (HIF-1), a member of the rapidly growing Per-ARNT-Sim (PAS) family of basic helix-loop-helix (bHLH) transcription factors (Semenza, J. Clin. Invest., 106, 809–812, 2000). HIF-1 exists as an $\alpha\beta$ heterodimer, the activation of which is dependent upon stabilization of an $O_2$-dependent degradation domain of the $\alpha$ subunit by the ubiquitin-proteasome pathway (Huang et al., Proc. Nat. Acad. Sci. (USA), 95, 7987–7992, 1998). Binding of HIF-1 to DNA consensus domains (5'-RCGTG-3') (SEQ ID NO: 25) results in the transcriptional induction of HIF-1-bearing gene promoters (Semenza, Curr. Opin. Genet Dev., 8, 588–594, 1998). A functional hypoxia response element/ enhancer (HRE) is defined by the central HIF-1 binding site and flanking nucleotides surrounding this site.

In the course of these studies, computer search analysis of the mdr1 gene identified 11 previously unappreciated HIF-1 binding site in the published mdr1 gene (Ueda et al., J. Biol. Chem., 262, 17432–17436, 1987; Chen et al., J. Biol. Chem., 265, 506–514, 1990), each of which are unique to mdr1.

These sequences, with flanking nucleotides, are shown below (central HIF-1 binding site in bold caps; the position is relative to transcription start site):

ctttgaaagACGTGtctacataag with HIF-1 site at positions −256 to −260 (SEQ ID NO: 26)

cagcgccgggGCGTGggctgagcac with HIF-1 site at positions −45 to −49 (SEQ ID NO: 27)

aactctgcctTCGTGgagatgctgg with HIF-1 site at positions +498 to +502 (SEQ ID NO: 28)

taggatttacACGTGgttggaagct with HIF-1 site at positions +766 to +770 (SEQ ID NO: 29)

ttcgctatggCCGTGaaaatgtcac with HIF-1 site at positions +1612 to +1616 (SEQ ID NO: 30)

tcgccattgcACGTGccctggttcg with HIF-1 site at positions +1765 to +1769 (SEQ ID NO: 31)

gtaggagtgtCCGTGgatcacaagc with HIF-1 site at positions +2156 to +2160 (SEQ ID NO: 32)

ttggtgccatggCCGTGgggcaagtc with HIF-1 site at positions +3100 to +3104 (SEQ ID NO: 33)

cacctgggcaTCGTGTcccaggagcc with HIF-1 site at positions +3484 to +3488 (SEQ ID NO: 34)

caggaagagaTCGTGagggcagcaa with HIF-1 site at positions +3573 to +3577 (SEQ ID NO: 35)

cattgccatagcTCGTGcccttgttagac with HIF-1 site at positions +3701 to +3705 (SEQ ID NO: 36)

EXAMPLE 3

Functional Analysis of HRE in mdr1 Gene

Two approaches were utilized to analyze the role of HIF-1 in hypoxia-inducible mdr1 expression.

First, antisense oligonucleotides directed against HIF-1 were utilized to block HIF-1 expression and the influence on mdr1 induction in hypoxia was assessed. HIF-1$\alpha$ depletion in epithelial cells was accomplished by using antisense oligonucleotide loading as described previously (Caniggia et al., J. Clin. Invest, 105, 577–587, 2000) using phosphorothioate derivatives of antisense (GCC GGC GCC CTC CAT) (SEQ ID NO: 47) or control sense (ATG GAG GGC GCC GGC) ) (SEQ ID NO: 48) oligonucleotides. Antisense oligonucleotide treatment of subconfluent epithelial cells was done as described previously (Colgan et al., J. Exp. Med., 184, 1003–1015, 1996), with modifications. T84 epithelial cells were washed in serum free media then in media containing 20 μg/ml Geneporter transfection reagent (Gene Therapy Systems, San Diego, Calif.) with 2 μg/ml HIF-1$\alpha$ antisense or sense oligonucleotide. Cells were incubated for 4h at 37° C. then replaced with serum containing growth media. Treated cells were exposed to hypoxia or normoxia for indicated periods of time. mdr1 or HIF-1$\alpha$ mRNA were quantified by RT-PCR. The directed loss of HIF-1$\alpha$ through antisense oligonucleotides resulted in the significant downregulation of basal (i.e. normoxic cells) mdr1 mRNA expression, and a complete loss of hypoxia inducibility.

As a second approach, luciferase reporter constructs expressing varied lengths of the mdr1 promoter were utilized to address hypoxia inducibility. CaCO2 cells were used to assess mdr1 inducibility by hypoxia. Plasmids expressing sequence corresponding to wild-type mdr1 (−189 to +133), truncations at the 3' end (−189 to +4), truncations at the 5' end (−2 to +133) or internal truncations (−119 to +4) of the promoter, using standard methods of overnight transfection utilizing Effectene transfection reagent (Qiagen, Valencia, Calif.). After transfection, cells were subjected to hypoxia or normoxia for 24 hrs. Luciferase activity was assessed (Topcount-NXT, Hewlett-Packard) utilizing a luciferase assay kit (Stratagene, La Jolla, Calif.). All luciferase activity was normalized to total cellular protein. Cells expressing the wild-type mdr1 promoter (nucleotides−189 to +133) showed a 2.5±0.3-fold increase in luciferase activity when subjected to 24 hr hypoxia compared to normoxia controls (p<0.01). Constructs expressing truncations at the 3' end (−189 to +4) did not significantly influence hypoxia inducibility (P=not significant). Likewise, truncations at both the 3' and 5' end (−119 to +4) did not influence hypoxia inducibility. Conversely, constructs expressing a 5' truncation, which includes the HIF-1 binding site (located at positions −49 to −45) resulted in a complete abolition of hypoxia inducibility (P<0.001). Interestingly, and consistent with our findings with HIF-1 antisense oligonucleotides, expression of the truncated reporter construct lacking the HIF-1$\alpha$ binding site was significantly decreased in cells exposed to normoxia (P<0.025), suggesting a role for HIF-1 in constituitive mdr1 expression.

As an extension of these data, we assessed hypoxia inducibility using wild-type promoter constructs in cells depleted of HIF-1 through antisense oligonucleotides. Luciferase activity in under conditions of both hypoxia and normoxia was diminished compared to wild-type (P<0.025 for both hypoxia and normoxia compared to wild-type alone), providing further evidence for HIF-1 in both basal and hypoxia-induced expression of mdr1.

EXAMPLE 4 mdr1-HRE Antisense Oligonucleotides

The following antisense oligonucleotides have been synthesized as phosphorothioate derivatives and ongoing work utilizes these compounds to define basal and hypoxia-induced mdr1 expression levels.

ctt atg tag aca cgt ctt tca aag for HRE at positions −45 to −49 (SEQ ID NO: 9)

gtg ctc agc cca cgc ccc ggc gct g for HRE at positions −256 to −260 (SEQ ID NO: 10)

cca gca tct cca cga agg cag agt t for HRE at positions +498 to +502 (SEQ ID NO: 11)

agc ttc caa cca cgt gta aat cct a for HRE at positions +766 to +770 (SEQ ID NO: 12)

gtg aca ttt tca cgg cca tag cga a for HRE at positions +1612 to +1616 (SEQ ID NO: 13)

cga acc agg gca cgt gca atg gcg a for HRE at positions +1765 to +1769 (SEQ ID NO: 14)

gct tgt gat cca cgg aca ctc cta c for HRE at positions +2156 to +2160 (SEQ ID NO: 15)

EXAMPLE 5 mdr1-HRE binding site mutations: To rule out the possibility that truncations at the 5' end of the MDR promoter simply reflect the deletion of a large DNA segment, studies were done to examine the influence of HIF-1 binding site mutations on hypoxia inducibility. HIF-1 binding site mutations were introduced in the hypoxia inducible 3' end truncation (3'ΔMDR) and a triple nucleotide mutation (consensus motif 5'-GC<u>GTG</u>-3' mutated to 5'-GC<u>CAT</u>-3' within HIF-1 site) resulted in a 83±10% decrease in luciferase activity under hypoxic conditions (p<0.01). This same mutation also resulted in a 72±6% decrease in activity in normoxic cells (p<0.01). Similarly, a deletional mutation (loss of entire HIF-1 site) resulted in luciferase activity decreases of 96±11% and 94±4% in hypoxic and normoxic cells, respectively (p<0.001 for both). Such data confirmed the necessity for HIF-1α consensus motifs for hypoxia inducibility and identified a potential pathway for HIF-1 regulation in non-hypoxic conditions.

EXAMPLE 6

Multicellular spheroid model: To better approximate the hypoxia response in a 3-dimensional structure (Desoize et al., Anticancer Res., 18, 4147–4157, 1998), a multicellular spheroid model was developed and examined for sensitivity to the P-gp cytotoxic substrate doxorubicin. Confocal imaging of multicellular spheroids revealed a dome-like appearance of cell clusters in the x–z orientation. Such multicellular spheroids were then utilized to examine toxicity of the chemotherapeutic agent and P-gp substrate doxorubicin (Goldstein et al., Eur. J. Cancer, 6, 1039–50, 1996). The degree of cell death (measured as the number of intact cells and reflected by increased BCECF labeling) was significantly decreased in cells subjected to either 24 (p<0.01) or 48 hr (p<0.001) periods of hypoxia. These data indicated that hypoxia provides a stimulus for the induction of the mdr1 gene as well as an increase in functional, surface expressed P-gp.

Posttranslational SUMOlation influences HIF-1α regulated gene expression. In order to test that HIF-1 is SUMO-1 modified, we conducted experiments which indicated an association of HIF-1α both with endogenous as well as epitope (hexahistidine)-tagged SUMO-1 HIF-1α induction was rapid and was detected by immunopecipitating SUMO-1. To further investigate the impact of SUMOlation on HIF-1 conveyed gene expression, we designed antisense oligonucleotides AS31(SEQ ID NO: 22), AS64 (SEQ ID NO: 23), and AS617 (SEQ ID NO: 24) directed against SUMO-1. Using these oligonucleotides we were able to modify the induction of HIF-1 in hypoxia. Thus, we were able to modify the HIF-1 conveyed hypoxia adaptive response by administration of sumo-1 antisense oligonucleotides.

I claim:

1. An isolated nucleic acid consisting of a sequence selected from the group consisting of: SEQ ID NOs. 9, 10, 11, 12, 13, 14, and 15.

2. A composition comprising an isolated nucleic acid of claim 1.

3. An isolated nucleic acid consisting of a full length complement of SEQ ID NOs. 9, 10, 11, 12, 13, 14, or 15.

4. A composition comprising an isolated nucleic acid of claim 3.

* * * * *